(12) United States Patent
Tachibana et al.

(10) Patent No.: US 11,814,368 B2
(45) Date of Patent: *Nov. 14, 2023

(54) TRIAZINE DERIVATIVES HAVING VIRUS REPLICATION INHIBITORY ACTIVITY AND PHARMACEUTICAL COMPOSITION COMPRISING THE SAME

(71) Applicants: Shionogi & Co., Ltd., Osaka (JP); NATIONAL UNIVERSITY CORPORATION HOKKAIDO UNIVERSITY, Hokkaido (JP)

(72) Inventors: Yuki Tachibana, Osaka (JP); Shota Uehara, Osaka (JP); Yuto Unoh, Osaka (Continued)

(73) Assignees: SHIONOGI & CO., LTD., Osaka (JP); NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 73 days.

This patent is subject to a terminal disclaimer.

(21) Appl. No.: 17/733,366

(22) Filed: Apr. 29, 2022

(65) Prior Publication Data
US 2023/0212154 A1 Jul. 6, 2023

Related U.S. Application Data

(63) Continuation of application No. PCT/JP2022/006496, filed on Feb. 17, 2022.

(30) Foreign Application Priority Data

Apr. 14, 2021 (JP) ................................. 2021-068672
(Continued)

(51) Int. Cl.
*C07D 403/14* (2006.01)
*A61P 31/14* (2006.01)
(Continued)

(52) U.S. Cl.
CPC .............. *C07D 403/14* (2013.01); *A61K 31/53* (2013.01); *A61K 47/542* (2017.08);
(Continued)

(58) Field of Classification Search
CPC ..... C07D 403/14; A61K 31/53; A61K 47/542;
(Continued)

(56) References Cited

U.S. PATENT DOCUMENTS

2011/0319414 A1 12/2011 Kai et al.
2013/0172317 A1 7/2013 Kai et al.
(Continued)

FOREIGN PATENT DOCUMENTS

CN 113620888 11/2021
CN 113666914 11/2021
(Continued)

OTHER PUBLICATIONS

Maren de Vries et al., "A Comparative Analysis of SARS-CoV-2 Antivirals Characterizes 3CL$^{pro}$ Inhibitor PF-00835231 as a Potential New Treatment for COVID-19", Journal of Virology, vol. 95, issue 10, e01819-20, pp. 1-22, Apr. 26, 2021, <URL: https://journals.asm.org/doi/10.1128/JVI.01819-20><doi: 10.1128/JVI.01819-20>.
(Continued)

*Primary Examiner* — Shengjun Wang
(74) *Attorney, Agent, or Firm* — Wenderoth, Lind & Ponack, L.L.P.

(57) ABSTRACT

The present invention provides a compound exhibiting coronavirus 3 CL protease inhibitory activity or a pharmaceutically acceptable salt thereof, and a pharmaceutical composition comprising the same. Furthermore, the present invention provides a crystalline form useful as an active pharmaceutical ingredient, and a pharmaceutical composition comprising the same.
(Continued)

A compound represented by Formula:

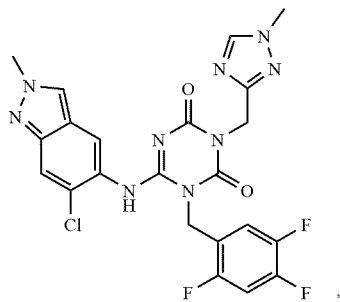

or a pharmaceutically acceptable salt thereof.

15 Claims, 13 Drawing Sheets

Specification includes a Sequence Listing.

(72) Inventors: (JP); Kenji Nakahara, Osaka (JP); Yoshiyuki Taoda, Osaka (JP); Yukiko Yamatsu, Osaka (JP); Shigeru Ando, Osaka (JP); Michihito Sasaki, Hokkaido (JP)

(30) Foreign Application Priority Data

Jun. 25, 2021 (JP) .................................. 2021-105802
Sep. 22, 2021 (JP) .................................. 2021-153819

(51) Int. Cl.
*A61K 31/53* (2006.01)
*A61K 47/54* (2017.01)

(52) U.S. Cl.
CPC .................................. *A61P 31/14* (2018.01)

(58) Field of Classification Search
CPC ...................................................... A61P 31/14
See application file for complete search history.

(56) References Cited

U.S. PATENT DOCUMENTS

| | | | |
|---|---|---|---|
| 2013/0225596 A1 | 8/2013 | Kai et al. |
| 2016/0024072 A1 | 1/2016 | Kai et al. |
| 2016/0052892 A1 | 2/2016 | Kai et al. |
| 2016/0115151 A1 | 4/2016 | Kai |
| 2016/0185736 A1 | 6/2016 | Kai et al. |
| 2017/0298058 A1 | 10/2017 | Kai et al. |
| 2017/0362199 A1 | 12/2017 | Kai |

FOREIGN PATENT DOCUMENTS

| | | |
|---|---|---|
| CN | 113735838 | 12/2021 |
| CN | 113773300 | 12/2021 |
| CN | 113801097 | 12/2021 |
| WO | 2010/092966 | 8/2010 |
| WO | 2012/009258 | 1/2012 |
| WO | 2012/020742 | 2/2012 |
| WO | 2012/020749 | 2/2012 |
| WO | 2013/089212 | 6/2013 |
| WO | 2013/118855 | 8/2013 |
| WO | 2014/200078 | 12/2014 |
| WO | 2021/205298 | 10/2021 |
| WO | 2021/250648 | 12/2021 |

OTHER PUBLICATIONS

"Aerosol and Surface Stability of SARS-CoV-2 as Compared with SARS-CoV-1", The New England Journal of Medicine, Apr. 16, 2020, vol. 38;16, pp. 1564-1567.

"COVID-19 Dashboard by the Center for Systems Science and Engineering at Johns Hopkins University", [online], Johns Hopkins University [searched on Jan. 28, 2022], URL:https://coronavirus.jhu.edu/map.html, 1 page.

"Pfizer's Novel COVID-19 Oral Antiviral Treatment Candidate Reduced Risk Of Hospitalization Or Death By 89% in Interim Analysis of Phase 2/3 EPIC-HR Study", Pfizer Press Release, Nov. 5, 2021, searched online Feb. 15, 2022, URL:https://www.pfizer.com/news/press-release/press-release-detail/pfizers-novel-covid-19-oral-antiviral-treatment-candidate, pp. 1-10.

"Report of the WHO-China Joint Mission on Coronavirus Disease 2019 (COVID-19)", WHO, dated Feb. 16-24, 2020, searched on Feb. 8, 2021, URL:https://www.who.int/docs/default-source/coronaviruse/who-china-joint-mission-on-covid-19-final-report.pdf, pp. 1-40.

Anand, K. et al, "Coronavirus Main Proteinase (3CL$^{pro}$) Structure: Basis for Design of Anti-SARS Drugs", Science, Jun. 13, 2003, vol. 300, pp. 1763-1767.

Andreas Luttens et al., "Ultralarge Virtual Screening Identifies SARS-CoV-2 Main Protease Inhibitors with Broad-Spectrum Activity against Coronaviruses", J. Am. Chem. Soc., 2022, vol. 144, pp. 2905-2920.

Atassi, G et al., "Preclinical evaluation of antitumor activity of new epoxide derivatives", Contributions to Oncology (1984) vol. 18, pp. 221-234.

Atassi, G et al., "Preclinical evaluation of the anti tumour activity of new epoxyde derivatives", Cancer Treatment Reviews (1984), vol. 11, Supplement A, pp. 99-110.

Chunlong Ma et al., "Boceprevir, GC-376, and calpain inhibitors II, XII inhibit SARS-CoV-2 viral replication by targeting the viral main protease", Cell Research, May 2020, vol. 30, pp. 678-692.

Dafydd Owen, "Oral inhibitors of the SARS-CoV-2 main protease for the treatment of COVID-19", ACS Spring Meeting 2021, Virtual, Abstract 243, Apr. 6-May 2, 2021.

Dafydd R. Owen et al., "An oral SARS-CoV-2 M$^{pro}$ inhibitor clinical candidate for the treatment of COVID-19", Science (2021), vol. 374, pp. 1586-1593.

Fischer, H. et al., "Investigation of the antitumor activity of new epoxide derivatives. Part II: N-Glycidylated oxo-nitrogen heterocycles", Arzneimittel-Forschung (1984), vol. 34, issue 6, pp. 663-668.

International Search Report dated Apr. 26, 2022 in International (PCT) Application No. PCT/JP2022/006496, with English translation.

Kenichi Akaji et al., "Design and Evaluation of Anti-SARS-Coronavirus Agents Based on Molecular Interactions with the Viral Protease", Molecules, 2020, vol. 25, 3920, pp. 1-19.

Michihito Sasaki et al., "Oral administration of S-217622, a SARS-CoV-2 main protease inhibitor, decreases viral load and accelerates recovery from clinical aspects of COVID-19", pp. 1-51 (Feb. 15, 2022).

Olujide O. Olubiyi et al., "High Throughput Virtual Screening to Discover Inhibitors of the Main Protease of the Coronavirus SARS-CoV-2", Molecules, 2020, vol. 25, 3193, pp. 1-20.

Patent Search Report issued in a counterpart Chinese Patent Application No. 2022107421862, with English language translation (Feb. 28, 2023).

STN Registry, L1 Answer 1 Of 1, Pages 1-3, RN 2647530-73-0, PX1_STN_RN 2647530 (Jun. 16, 2021).

Unoh, Y., et al., "Discovery of S-217622, a Non-Covalent Oral SARS-CoV-2 3CL Protease Inhibitor Clinical Candidate for Treating COVID-19", bioRxiv preprint doi: https://doi.org/10.1101/2022.01.26.477782, Jan. 26, 2022, pp. 1-52.

Unoh, Y., et al., "Discovery of S-217622, a Noncovalent Oral SARS-CoV-2 3CL Protease Inhibitor Clinical Candidate for Treating COVID-19", J. Med. Chem., 2022, Vol. 65, pp. 6499-6512.

(56) References Cited

OTHER PUBLICATIONS

Written Opinion of the International Searching Authority dated Apr. 26, 2022 in International (PCT) Application No. PCT/JP2022/006496, with English translation.

Yuzhi Liu et al., "The development of Coronavirus 3C-Like protease ($3CL^{pro}$) inhibitors from 2010 to 2020", European Journal of Medicinal Chemistry, 2020, vol. 206, 112711, pp. 1-18.

Zhang, Chun-Hui et al., "Potent Noncovalent Inhibitors of the Main Protease of SARS-CoV-2 from Molecular Sculpting of the Drug Perampanel Guided by Free Energy Perturbation Calculations", ACS Central Science (2021), vol. 7, No. 3, pp. 467-475.

Zhang, L. et al., "Crystal structure of SARS-CoV-2 main protease provides a basis for design of improved a-ketoamide inhibitors", Science (2020), vol. 368, pp. 409-412.

[Figure 1]
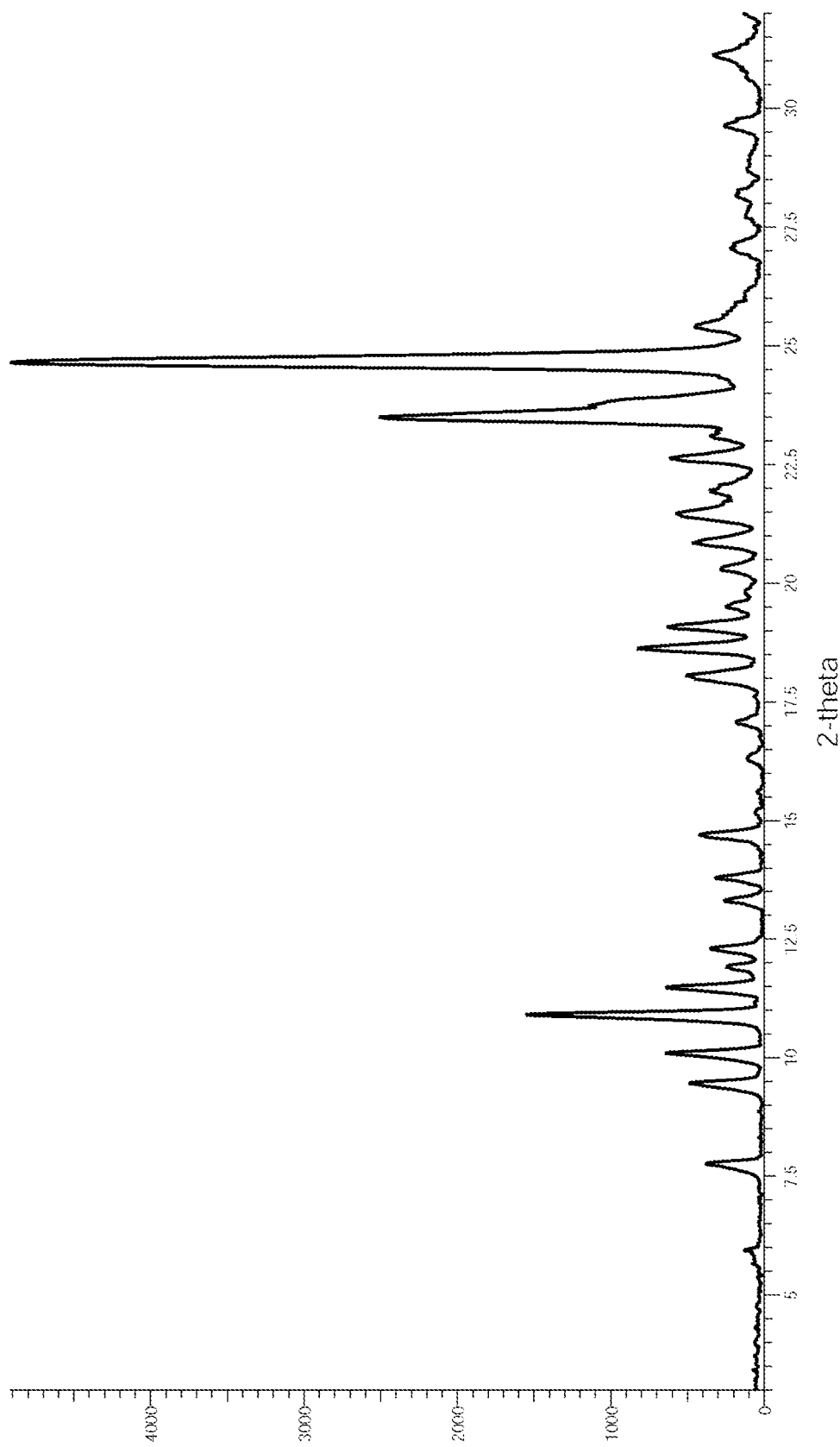

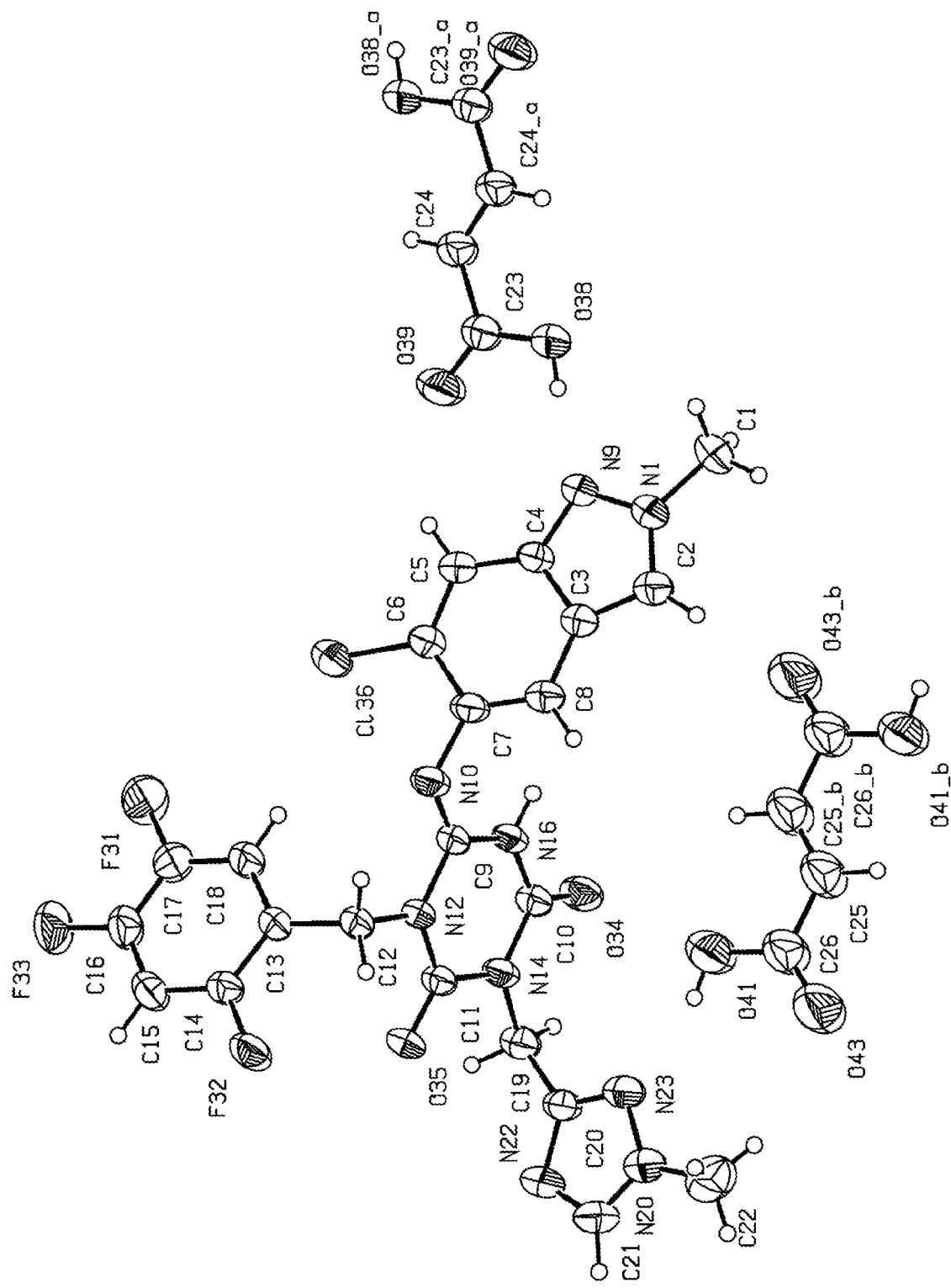
[Figure 2]

[Figure 3]
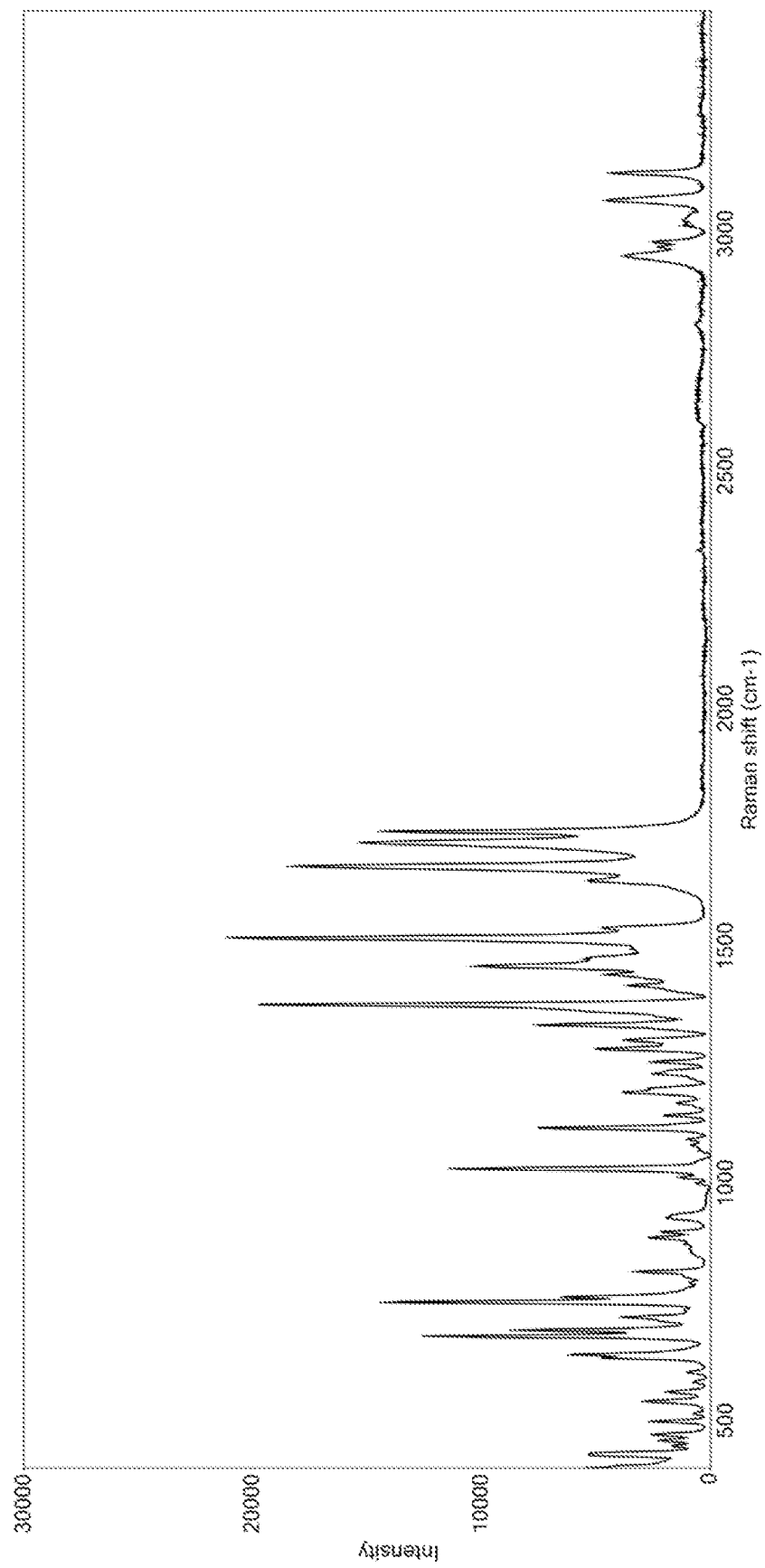

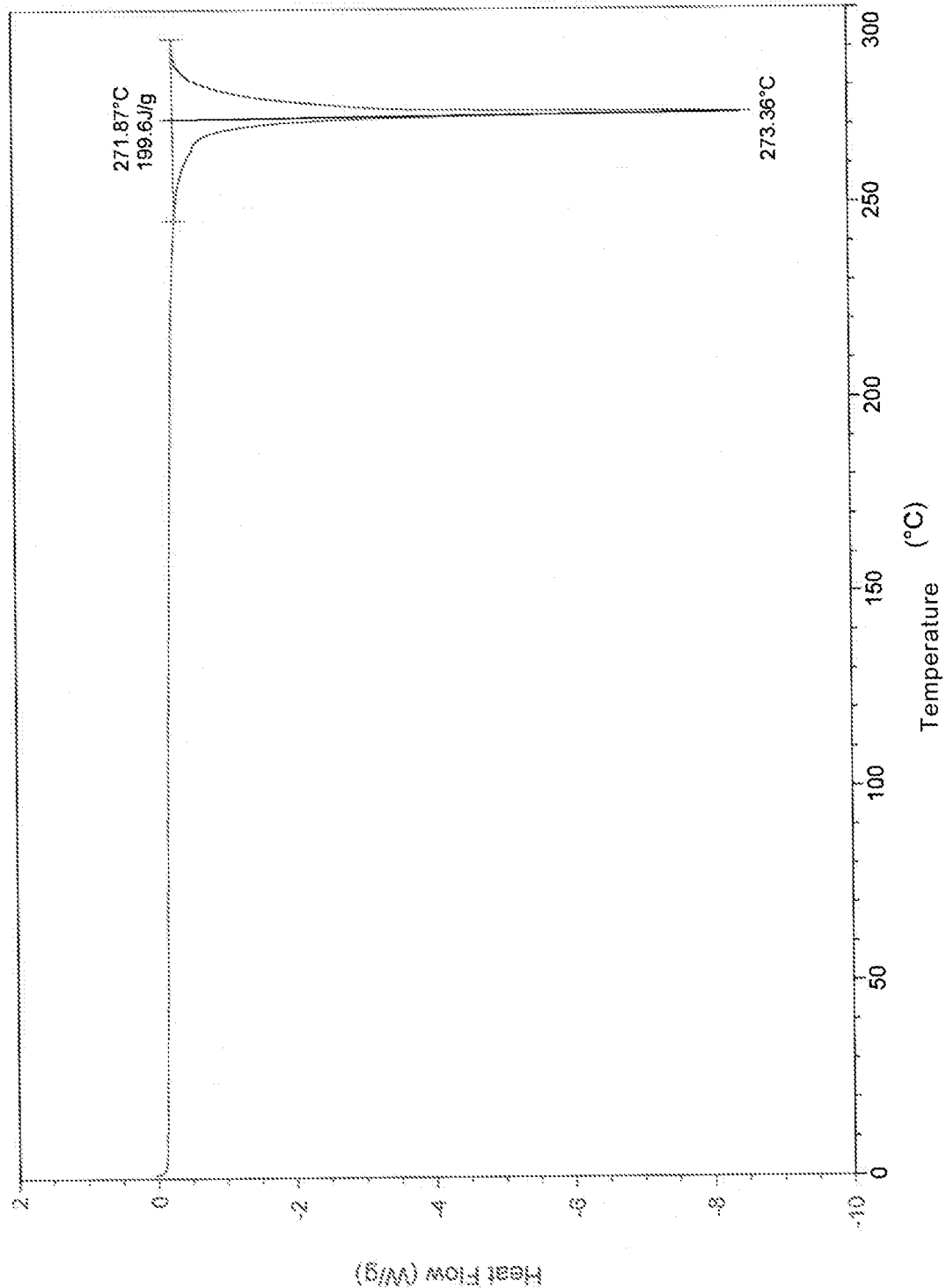
[Figure 4]

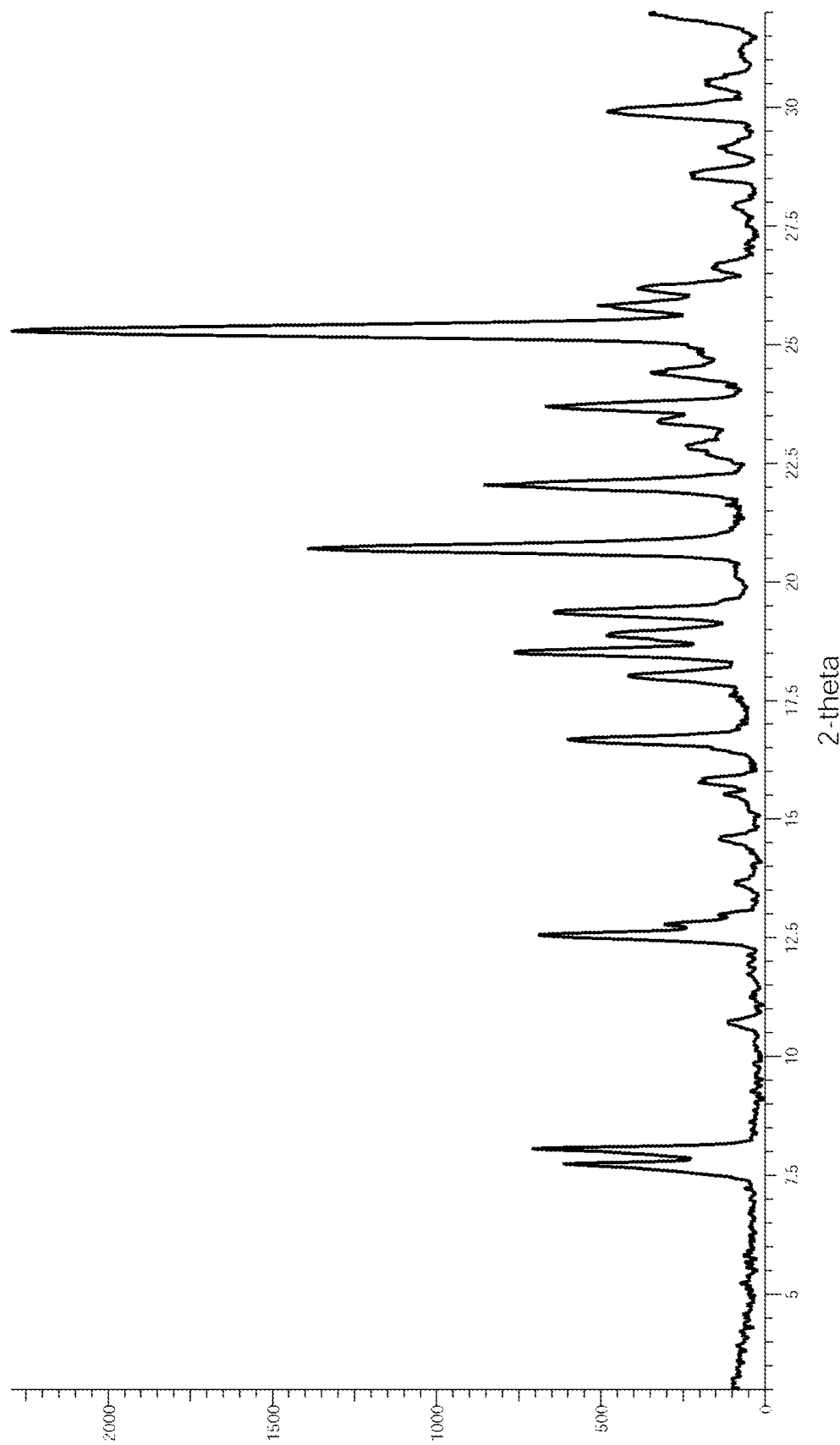
[Figure 5]

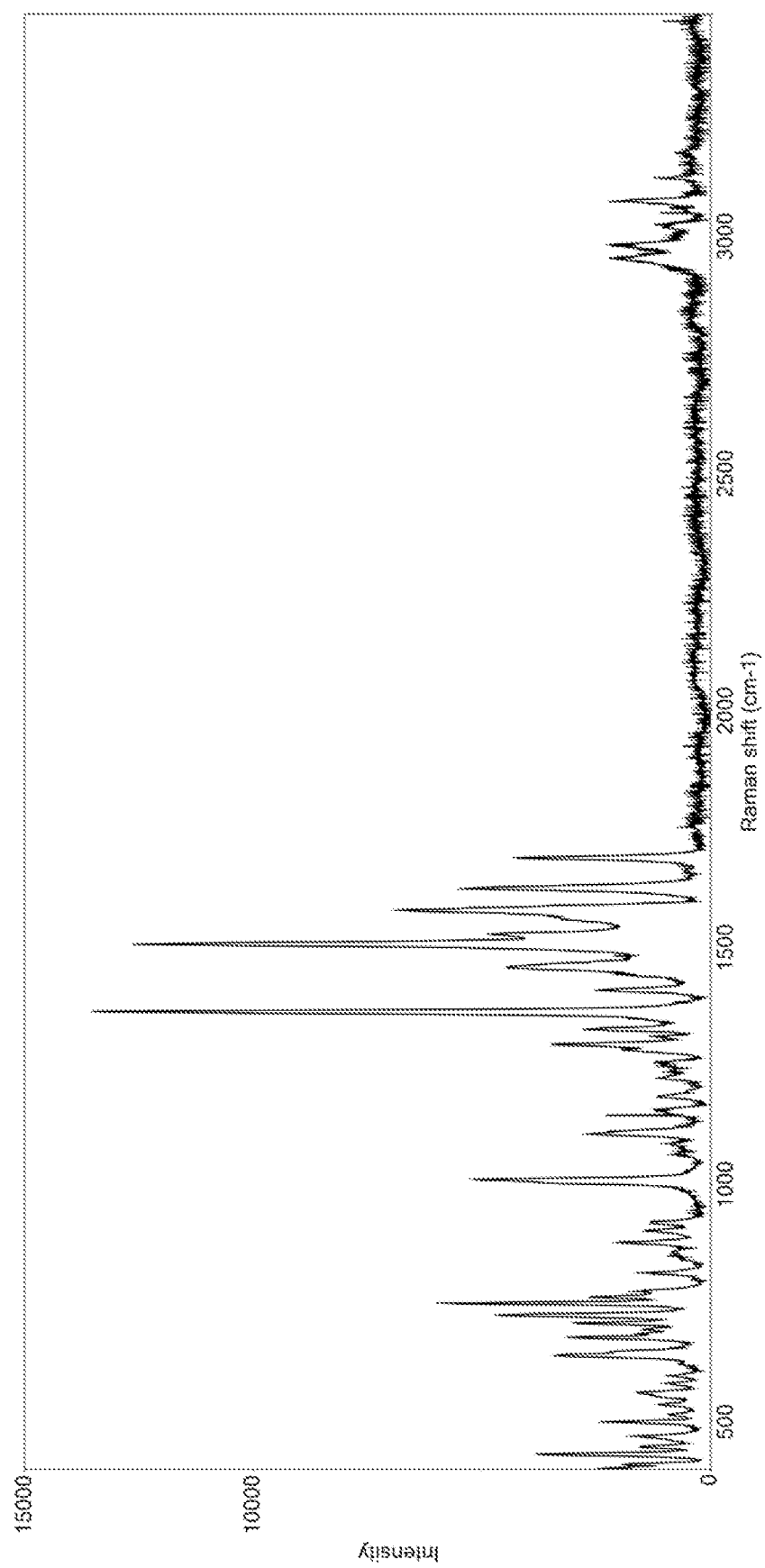
[Figure 6]

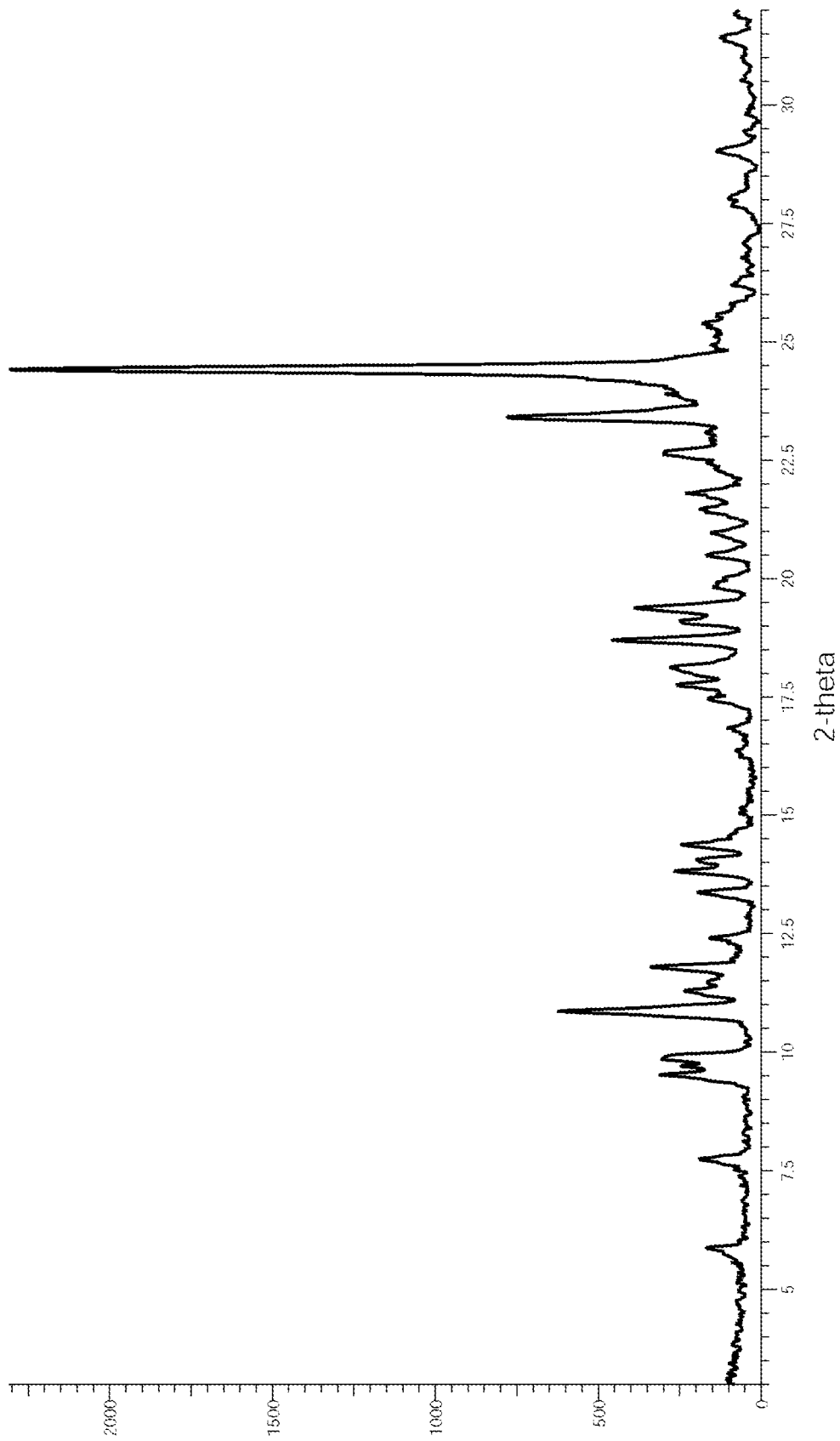
[Figure 7]

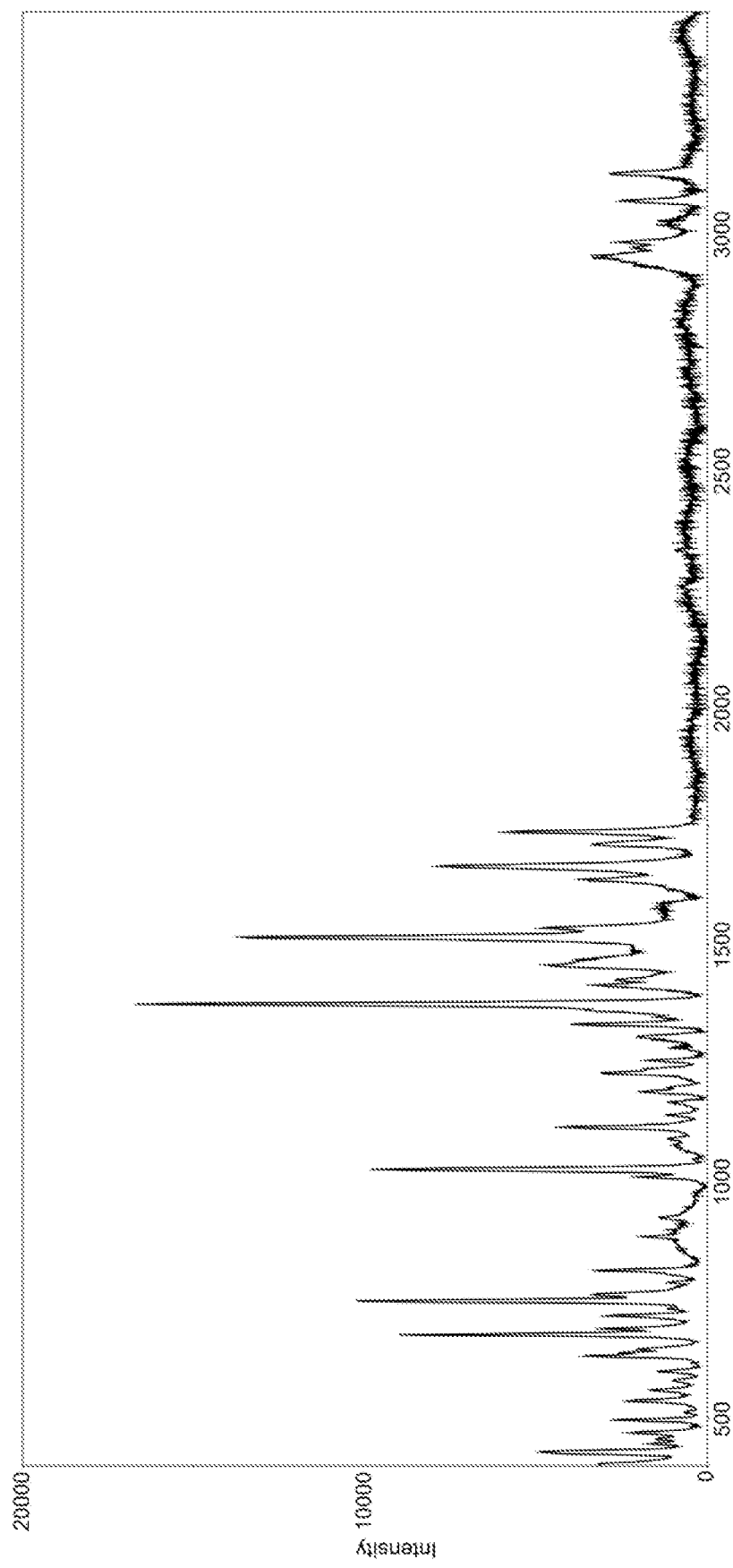
[Figure 8]

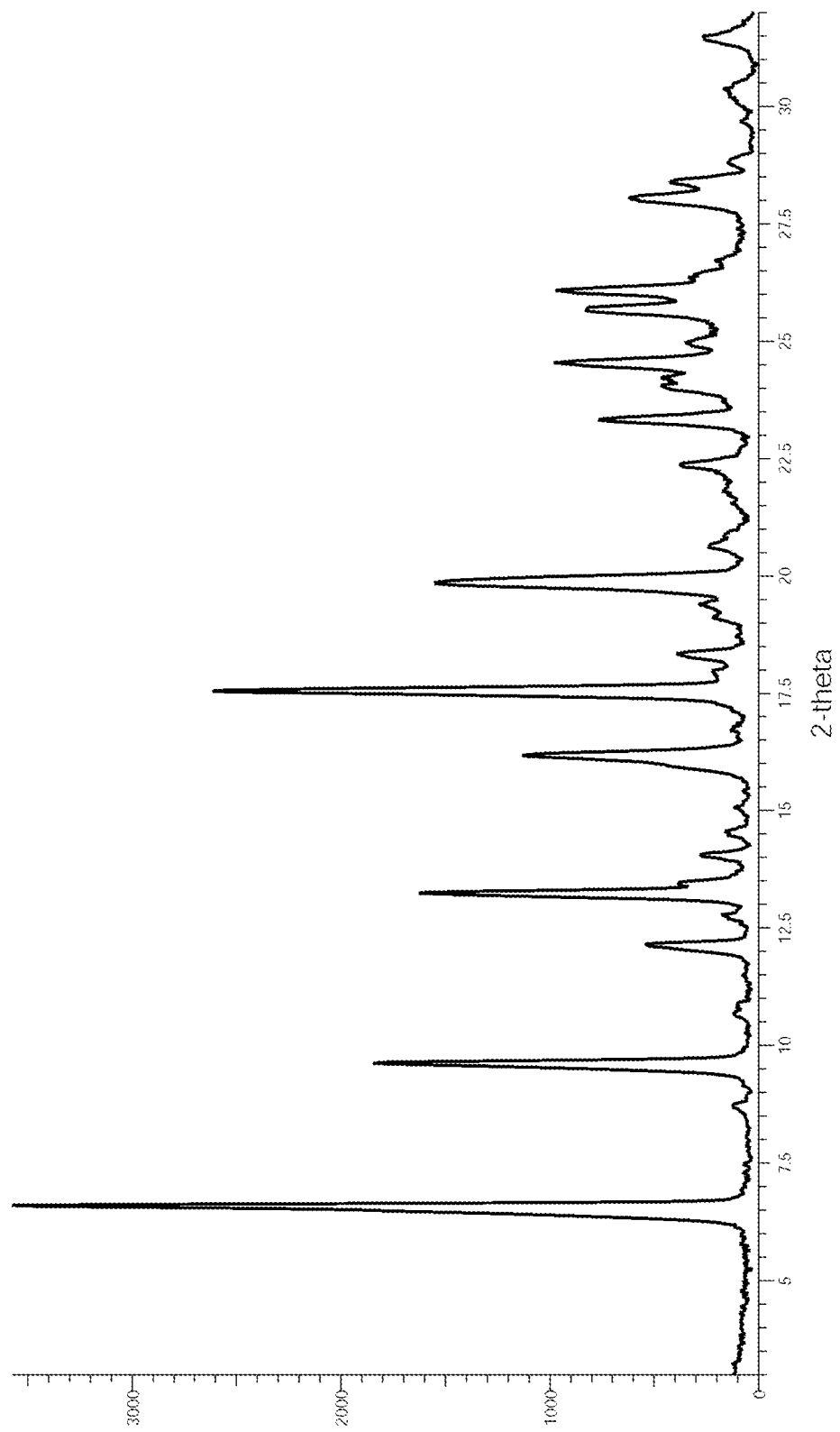
[Figure 9]

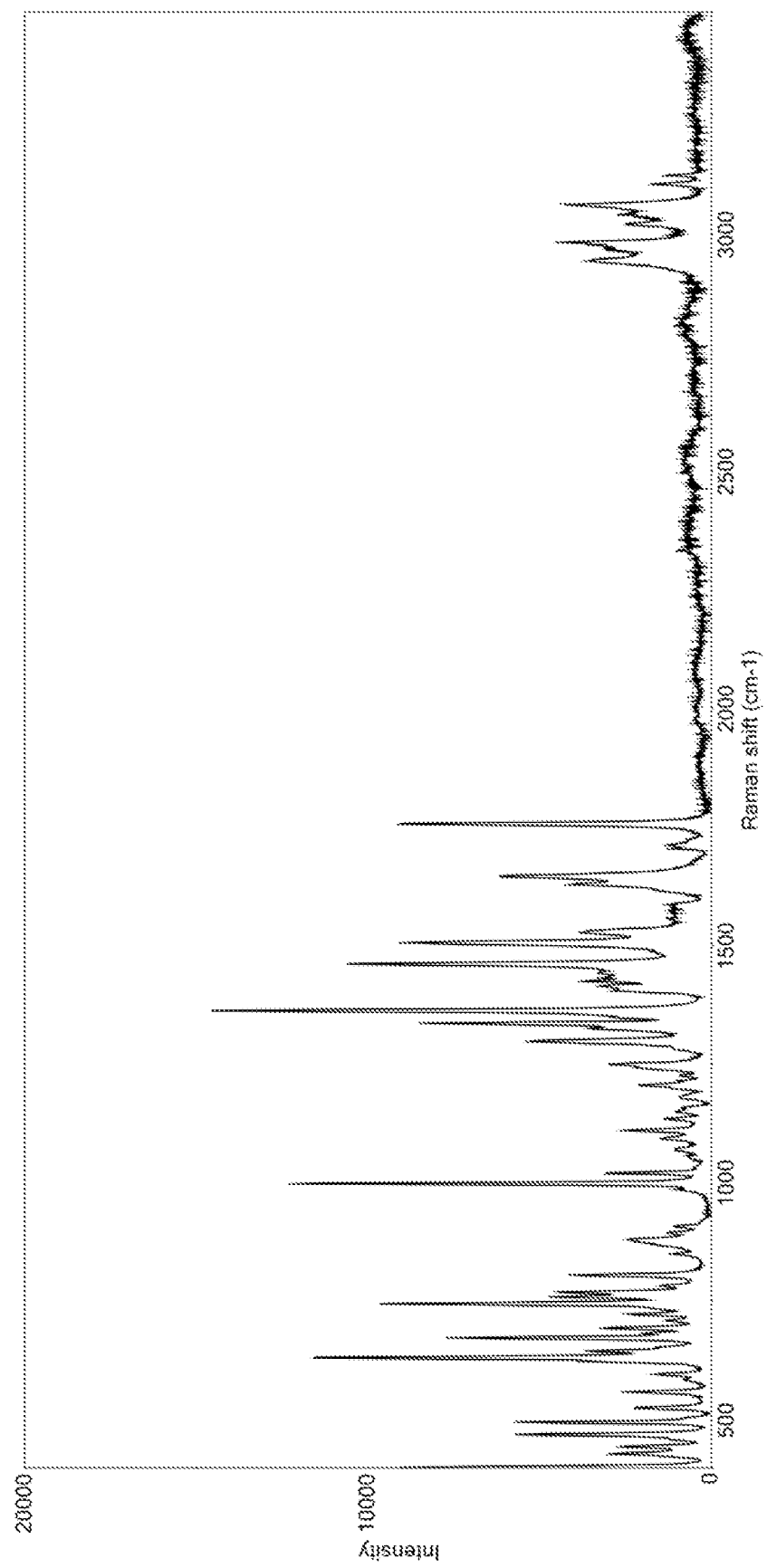
[Figure 10]

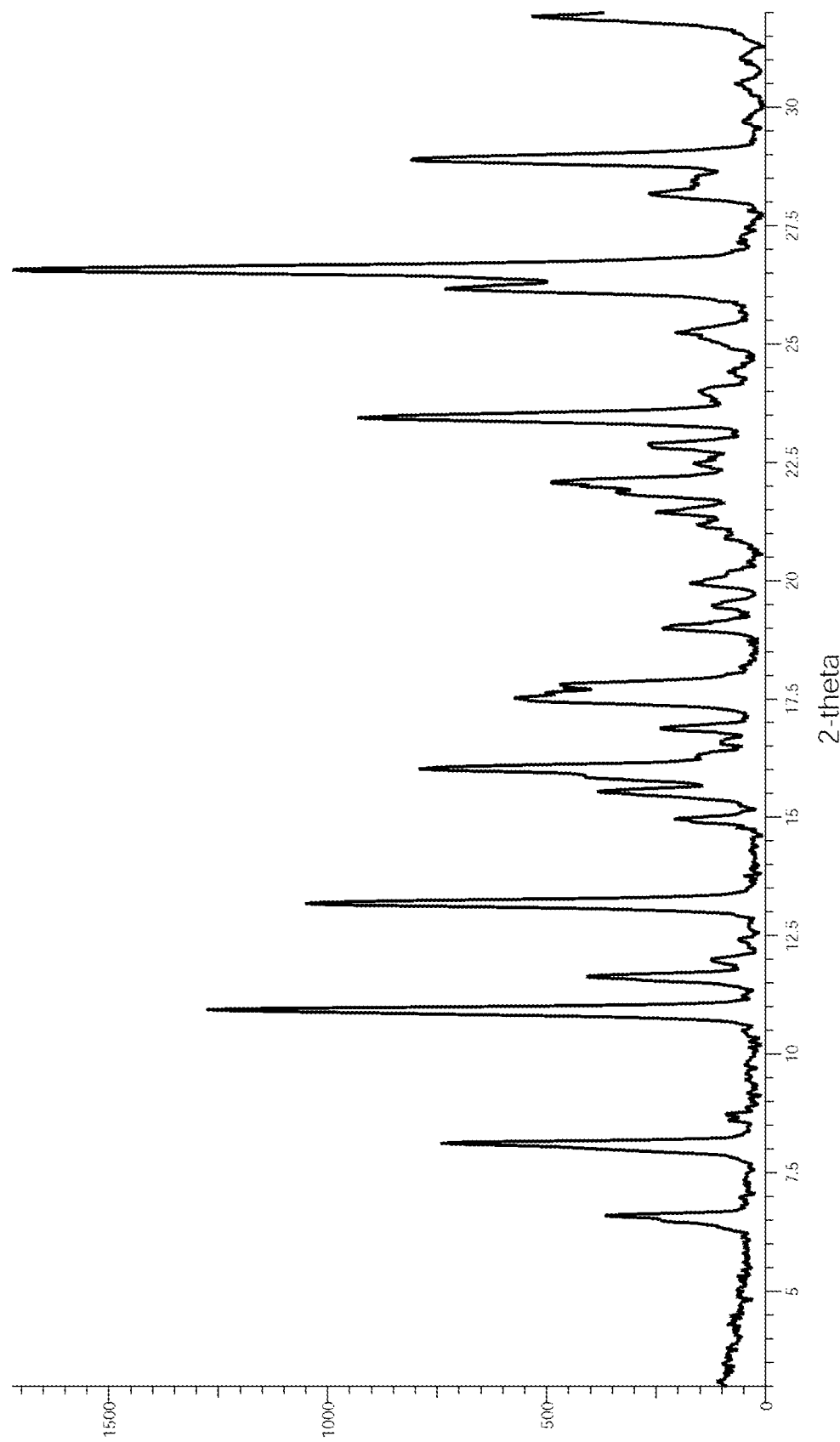
[Figure 11]

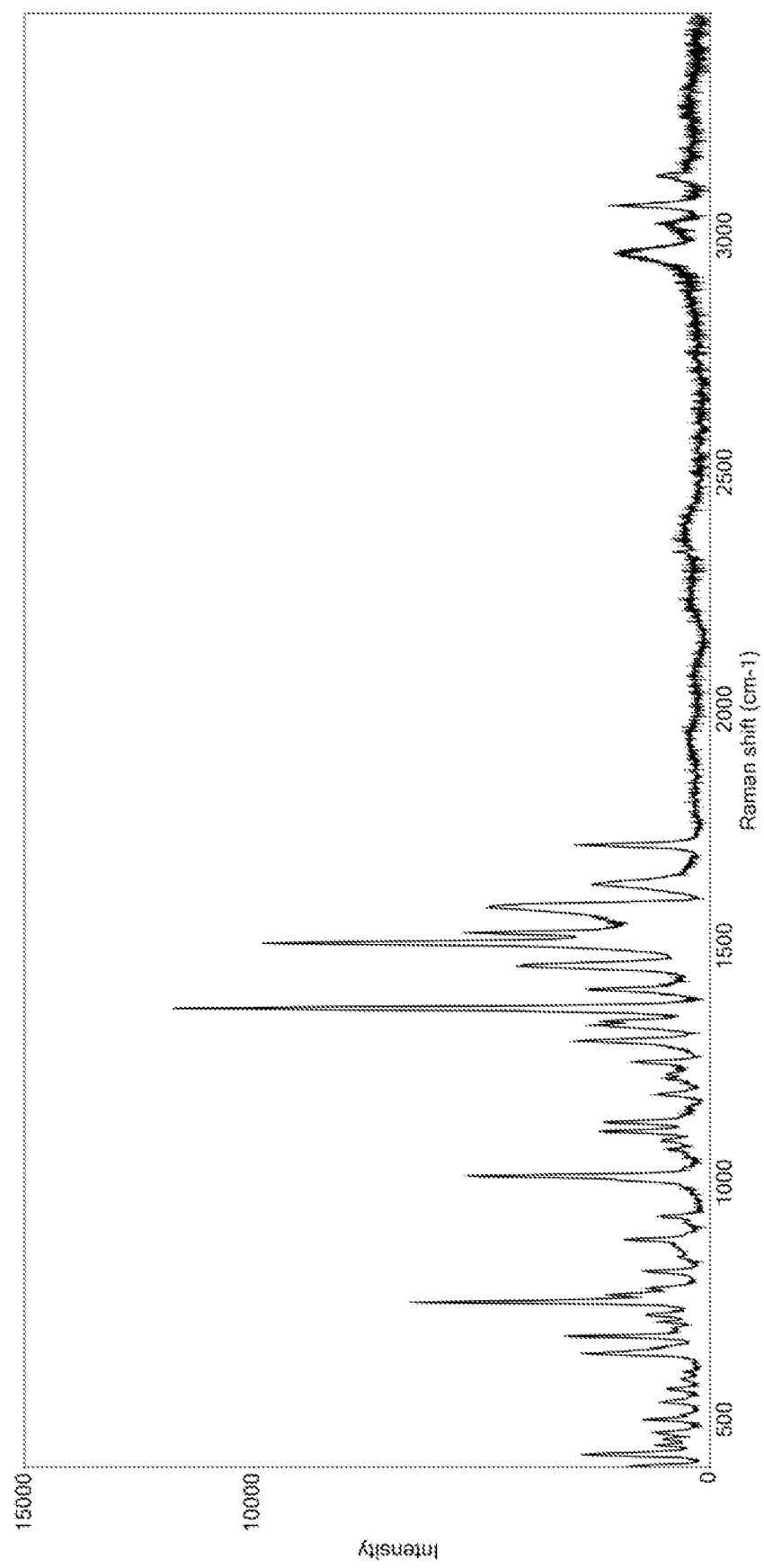
[Figure 12]

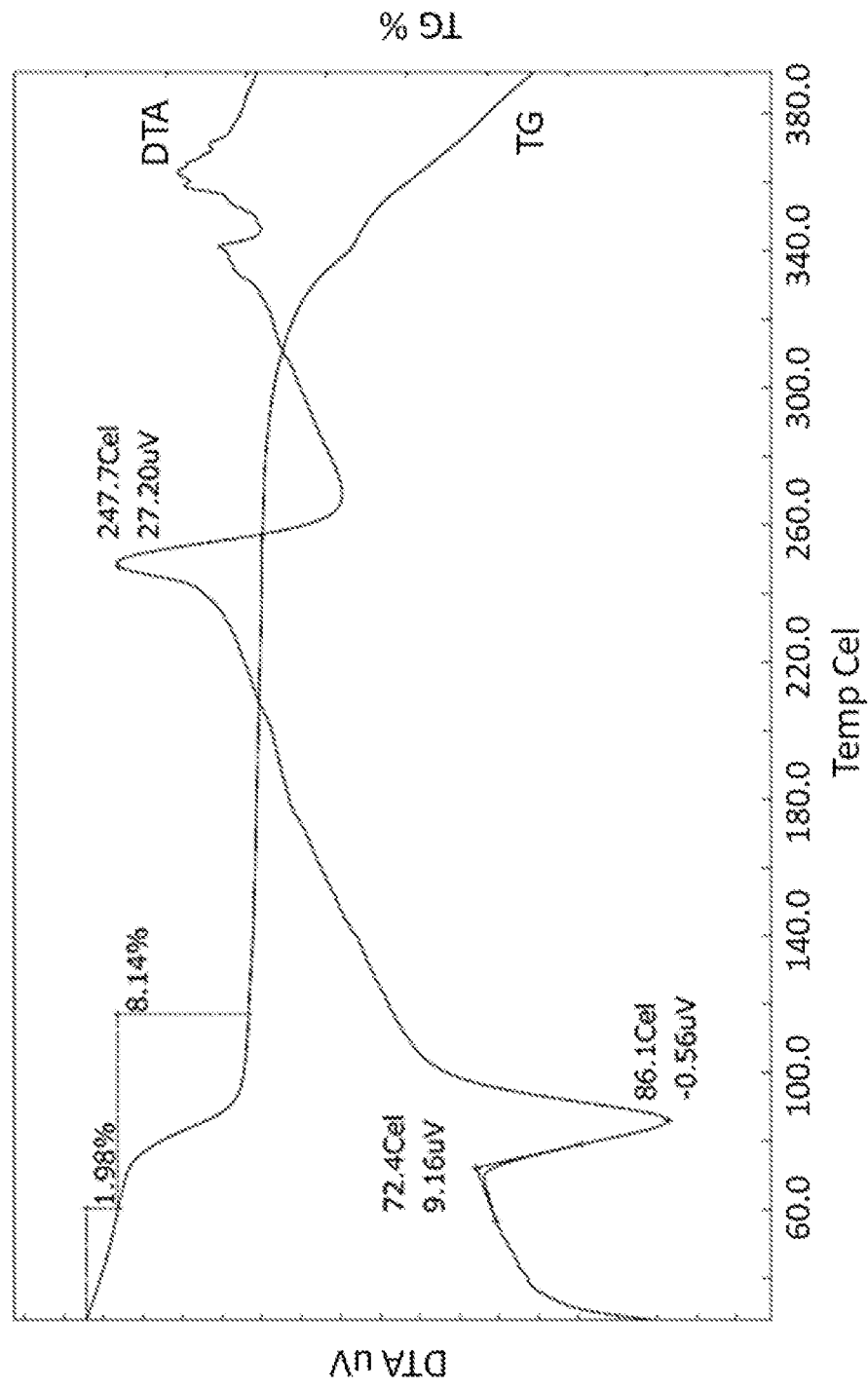
[Figure 13]

SEQUENCE LISTING

```
<160> NUMBER OF SEQ ID NOS: 2

<210> SEQ ID NO 1
<211> LENGTH: 14
<212> TYPE: PRT
<213> ORGANISM: Artificial sequence
<220> FEATURE:
<223> OTHER INFORMATION: Substrate Peptide

<400> SEQUENCE: 1

Glu Met Lys Arg Phe Gly Ser Gln Leu Val Ala Ser Thr Lys
1               5                   10

<210> SEQ ID NO 2
<211> LENGTH: 7
<212> TYPE: PRT
<213> ORGANISM: Artificial sequence
<220> FEATURE:
<223> OTHER INFORMATION: Internal Standard Peptide

<400> SEQUENCE: 2

Gln Leu Val Ala Ser Thr Lys
1               5
```

TRIAZINE DERIVATIVES HAVING VIRUS REPLICATION INHIBITORY ACTIVITY AND PHARMACEUTICAL COMPOSITION COMPRISING THE SAME

TECHNICAL FIELD

The present invention relates to a compound exhibiting coronavirus 3CL protease inhibitory activity and a pharmaceutical composition comprising a compound exhibiting coronavirus 3CL protease inhibitory activity. Furthermore, the present invention relates to a crystal and a cocrystal of a compound or a pharmaceutically acceptable salt thereof, exhibiting 3CL protease inhibitory activity, and a pharmaceutical composition comprising the same.

BACKGROUND ART

Coronaviruses, which belong to the order Nidovirales, family Coronaviridae, and the subfamily Coronavirinae, are positive-sense single-stranded RNA viruses that have a genome size of about 30 kilobases and are the largest among the known RNA viruses. Coronaviruses are classified into four genera, namely, the genus Alphacoronavirus, Betacoronavirus, Gammacoronavirus, and Deltacoronavirus, and a total of seven types of coronaviruses, including two kinds in the genus Alphacoronavirus (HCoV-229E and HCoV-NL63) and five kinds in the genus Betacoronavirus (HCoV-HKU1, HCoV-OC43, SARS-CoV, MERS-CoV, and SARS-CoV-2), are known as coronaviruses that infect humans. Among these, four kinds (HCoV-229E, HCoV-NL63, HCobr-HKU1, and HCoV-OC43) are pathogens of common cold, while the other three kinds are severe acute respiratory syndrome (SARS) coronavirus (SARS-CoV), Middle East respiratory syndrome (MERS) coronavirus (MERS-CoV), and a novel coronavirus (SARS-CoV-2), all of which cause severe pneumonia.

Novel coronavirus infections (COVID-19) that occurred in Wuhan, China, in December 2019, rapidly spread to the international community, and the pandemic was announced by the WHO on Mar. 11, 2020. The number of infected people confirmed as of Jan. 28, 2022, was more than 360 million, and the number of deaths reached more than 5.63 million (Non-patent Document 1). Droplet infection, contact infection, and aerosol infection have been reported as main routes of infection of SARS-CoV-2, and it has been confirmed that SARS-CoV-2 continues to drift in air together with aerosols and maintains infectivity for about 3 hours (Non-patent Document 2). The incubation period is about 2 to 14 days, and cold-like symptoms such as fever (87.9%), dry cough (67.7%), malaise (38.1%), and phlegm (33.4%) are typical (Non-patent Document 3). In severe cases, respiratory failure due to acute respiratory distress syndrome, acute lung injury, interstitial pneumonia, and the like occurs. Furthermore, multiple organ failure such as renal failure and hepatic failure has also been reported.

In Japan, as a result of drug repositioning of existing drugs, remdesivir, which is an antiviral drug, dexamethasone, which is an anti-inflammatory drug, and baricitinib, which is an antirheumatic drug, have been approved as therapeutic agents against COVID-19, and in January 2022, tocilizumab, which is an anti-IL-6 receptor antibody, have been received additional approval. Furthermore, in July 2021, ronapreve (casirivimab/imdevimab), which is an antibody cocktail therapy, was approved as special case approval, in September 2021, sotrovimab was approved as special case approval, and in December 2021, molnupiravir was approved as special case approval. Sufficient evidence has not been obtained on the efficacy and safety of these drugs. Accordingly, it is imperative to create therapeutic agents against COVID-19.

Upon infection of cells, coronaviruses synthesize two polyproteins. In these two polyproteins, structural proteins for producing new viral particles, replication complexes producing viral genomes, and two proteases are included. Proteases play an indispensable role for cleaving the polyproteins synthesized by viruses and causing each of the proteins to function. Between these two proteases, 3CL protease (main protease) bears most of the cleavage of the polyproteins (Non-patent Document 4).

Regarding COVID-19 therapeutic agents targeting 3CL proteases, it was published in ClinicalTrials.gov that Phase 1b trials for Lufotrelvir (PF-07304814), which is a prodrug of PF-00835231, have been completed by Pfizer Inc (NCT04535167). Furthermore, in March 2021, Pfizer Inc. announced that Phase 1 trials for PF-07321332, a therapeutic agent against novel coronavirus infections, will be initiated. The structural formulae of PF-00835231, Lufotrelvir and PF-07321332 are as shown below, and these agents are different from the compound of the present invention in chemical structure (Non-patent Documents 5, 12 and 13 and Patent Documents 6 and 7).

PF-00835231:

[Chemical Formula 1]

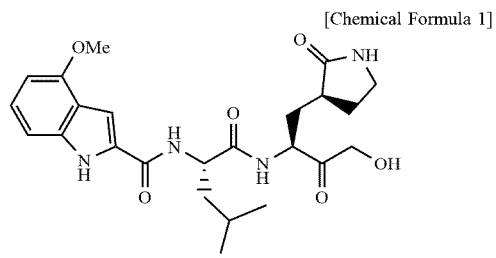

Lufotrelvir(PF-07304814):

[Chemical Formula 2]

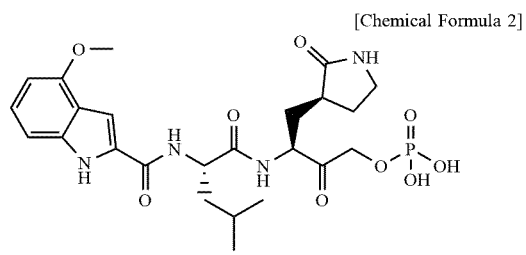

PF-07321332:

[Chemical Formula 3]

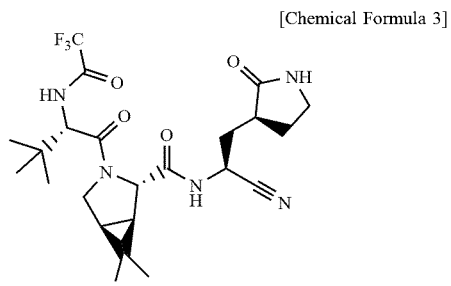

Furthermore, in July 2021, it was published in ClinicalTrials.gov that Phase 2/3 trials for a combination of PF-07321332 and ritonavir targeting COVID-19 patients with high-risk factors will be initiated (NCT04960202). Moreover, in November 2021, it was reported on the Pfizer website, PAXLOVID (TM) (PF-07321332; ritonavir) reduced the risk of hospitalization or death by 89% in high-risk adult patients compared to placebo (Non-Patent Document 14). Furthermore, in December 2021, PAXLOVID (TM) was approved for emergency use in the United States, and on Feb. 10, 2022, the Paxlovid® PACK was approved as special case approval in Japan.

Compounds having 3CL protease inhibitory activity are disclosed in Non-patent Documents 5 to 8; however, the compounds related to the present invention are neither described nor suggested in any of the documents.

Triazine derivatives and uracil derivatives having P2X$_3$ and/or P2X$_{2/3}$ receptor antagonistic activity have been disclosed in Patent Documents 1 to 4 and 8 to 12; however, the 3CL protease inhibitory activity and the antiviral effect are neither described nor suggested in any of the documents.

Triazine derivatives having antitumor effects have been disclosed in Non-patent Documents 9 to 11; however, the coronavirus 3CL protease inhibitory activity and the antiviral effects are described in none of the documents, and the compounds related to the present invention are neither described nor suggested in any of the documents.

Triazine derivatives having galanin receptor-regulating effects have been disclosed in Patent Document 5; however, the coronavirus 3CL protease inhibitory activity and the antiviral effects are not described in the document, and the compounds related to the present invention are neither described nor suggested in the documents.

PRIOR ART REFERENCES

Patent Document

[Patent Document 1] International Publication WO 2012/020749A
[Patent Document 2] International Publication WO 2013/089212A
[Patent Document 3] International Publication WO 2010/092966A
[Patent Document 4] International Publication WO 2014/200078A
[Patent Document 5] International Publication WO 2012/009258A
[Patent Document 6] International Publication WO 2021/205298A
[Patent Document 7] International Publication WO 2021/250648A
[Patent Document 8] China Patent Application Publication CN 113620888A
[Patent Document 9] China Patent Application Publication CN 113666914A
[Patent Document 10] China Patent Application Publication CN 113735838A
[Patent Document 11] Chinese Patent Application Publication CN 113773300A
[Patent Document 12] Chinese Patent Application Publication CN 113801097A Non-Patent Document

[Non-patent Document 1] "COVID-19 Dashboard by the Center for Systems Science and Engineering at Johns Hopkins University", [online], Johns Hopkins University, [retrieved on Jan. 28, 2022], Internet <URL: https://coronavirus.jhu.edu/map.html>.
[Non-patent Document 2] The NEW ENGLAND JOURNAL of MEDICINE (2020), Vol. 382, pp. 1564-1567.
[Non-patent Document 3] "Report of the WHO-China Joint Mission on Coronavirus Disease 2019 (COVID-19)", [online], Feb. 28, 2020, WHO, [retrieved on Feb. 8, 2021], Internet <URL: https://www.who.int/does/default-source/coronaviruse/who-chi-na-joint-mission-on-covid-19-final-report.pdf>.
[Non-patent Document 4] Science (2003), Vol. 300, pp. 1763-1767.
[Non-patent Document 5] "A comparative analysis of SARS-CoV-2 antivirals characterizes 3CLpro inhibitor PF-00835231 as a potential new treatment for COVID-19", Journal of Virology, Apr. 26, 2021, [retrieved on Feb. 15, 2022], Internet <URL: https://journals.asm.org/doi/10.1128./JVI.01819-20><doi. 10.1128/JVI.01819-20>.
[Non-patent Document 6] Cell Research (2020), Vol. 30, pp. 678-692.
[Non-patent Document 7] Science (2020), Vol. 368, pp. 409-412.
[Non-patent Document 8] ACS Central Science (2021), Vol. 7, No. 3, pp. 467-475.
[Non-patent Document 9] Cancer Treatment Reviews (1984), Vol. 11, Supplement 1, pp. 99-110.
[Non-patent Document 10] Contributions to Oncology (1984), Vol. 18, pp. 221-234.
[Non-patent Document 11] Arzneinittel-Forschung (1984), Vol. 11, No. 6, pp. 663-668.
[Non-patent Document 12] 261st Am Chem Soc (ACS) Natl Meet - 2021-04-05 / 2021-04-16 • Virtual, N/A • Abst 243
[Non-patent Document 13] Science (2021), Vol. 374, pp. 1586-1593.
[Non-patent Document 14] "Pfizer's Novel COVID-19 Oral Antiviral Treatment Candidate Reduced Risk Of Hospitalization Or Death By 89% In Interim Analysis Of Phase 2/3 EPIC-HR Study", [online], Nov. 5, 2021, Pfizer Press Release, [retrieved on Feb. 15, 2022], Internet <URL: https://www.pfizer.com/news/press-release/press-release-detail/pfizers-novel-covid-19-oral-antiviral-treatment-candidate>

SUMMARY OF THE INVENTION

Problems to be Solved by the Invention

An object of the present invention is to provide a compound having coronavirus 3CL protease inhibitory activity. Preferably, the present invention provides a compound having an antiviral activity, particularly a coronavirus replication inhibitory activity, and a medicament comprising the compound. Furthermore, another object of the present invention is to provide a crystalline form and a cocrystal of a compound or a pharmaceutically acceptable salt thereof, exhibiting 3CL protease inhibitory activity and a medicament containing the same.

Means for Solving the Problem

The present invention relates to the following. (1) A compound represented by Formula (I):

[Chemical Formula 4]

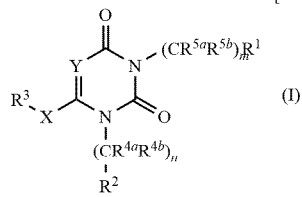

wherein
Y is N, or CR$^7$;
R$^7$ is a hydrogen atom, or substituted or unsubstituted alkyl;
R$^1$ is substituted or unsubstituted aromatic heterocyclyl, substituted or unsubstituted non-aromatic heterocyclyl, substituted or unsubstituted carbamoyl, or substituted or unsubstituted amino;

R² is substituted or unsubstituted aromatic carbocyclyl (provided that para-fluorophenyl, para-chlorophenyl, and para-methylphenyl are excluded), substituted or unsubstituted non-aromatic carbocyclyl, substituted or unsubstituted aromatic heterocyclyl, substituted or unsubstituted non-aromatic heterocyclyl, or substituted or unsubstituted alkyl;

R³ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

—X— is —NR⁶—, —CR⁶R⁶'—, —O—, —S—, or a single bond;

R⁶ and R⁶'are each independently a hydrogen atom, or substituted or unsubstituted alkyl;

m is 0, 1, or 2;

R⁵ᵃ is each independently a hydrogen atom, or substituted or unsubstituted alkyl;

R⁵ᵇ is each independently a hydrogen atom, or substituted or unsubstituted alkyl;

n is 0, 1, or 2;

R⁴ᵃ is each independently a hydrogen atom, or substituted or unsubstituted alkyl;

R⁴ᵇ is each independently a hydrogen atom, or substituted or unsubstituted alkyl;

provided that the following compounds are excluded:

[Chemical Formula 5]

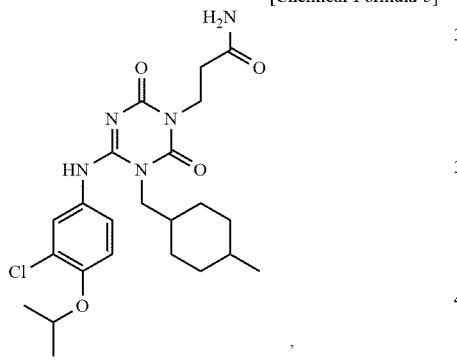

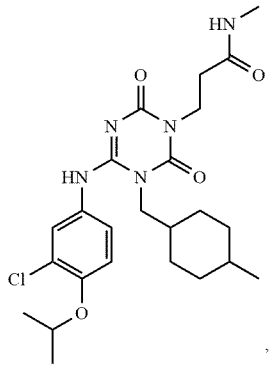

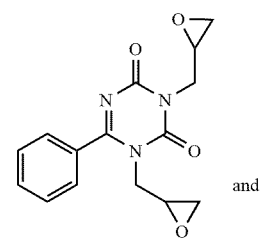

and

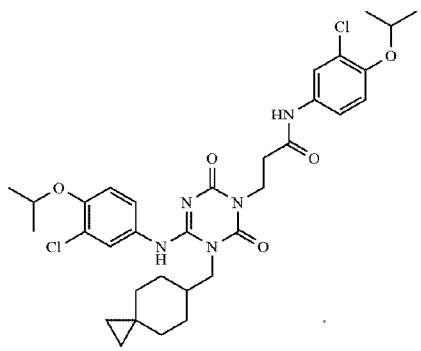

or a pharmaceutically acceptable salt thereof.

(AA1) A compound represented by Formula:

[Chemical Formula 6]

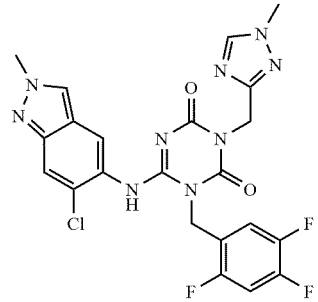

or a pharmaceutically acceptable salt thereof. (AA1') A compound represented by Formula:

[Chemical Formula 7]

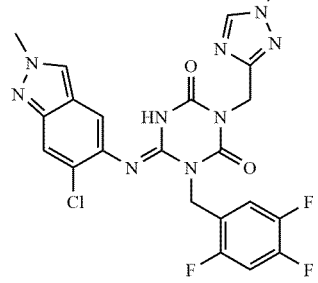

or a pharmaceutically acceptable salt thereof. (AA2) A pharmaceutical composition comprising the compound according to the above items (AA1) or (AA1'), or a pharmaceutically acceptable salt thereof. (AA3) A coronavirus 3CL protease inhibitor comprising the compound according to the above items (AA1) or (AA1'), or a pharmaceutically acceptable salt thereof.

(AA4) A coronavirus replication inhibitor comprising the compound according to the above items (AA1) or (AA1'), or a pharmaceutically acceptable salt thereof.

(AA5) The coronavirus replication inhibitor according to the above item (AA4), wherein the coronavirus is an alpha coronavirus and/or beta coronavirus.

(AA6) The coronavirus replication inhibitor according to the above item (AA4), wherein the coronavirus is SARS-CoV-2.

(AA7) A method for treating and/or preventing a disease associated with coronavirus 3CL proteases, characterized by administering the compound according to the above items (AA1) or (AA1'), or a pharmaceutically acceptable salt thereof.

(AA8) The compound according to the above items (AA1) or (AA1'), or a pharmaceutically acceptable salt thereof, for use in treating and/or preventing a disease associated with coronavirus 3CL proteases.

(1B) A complex comprising a compound represented by Formula (I-B):

[Chemical Formula 8]

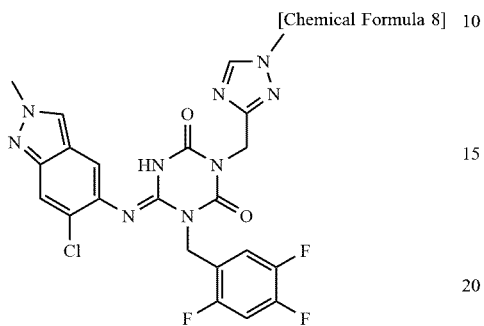

and fumaric acid.

(2B) The complex according to the above item (1B), wherein the compound represented by Formula (I-B):

[Chemical Formula 9]

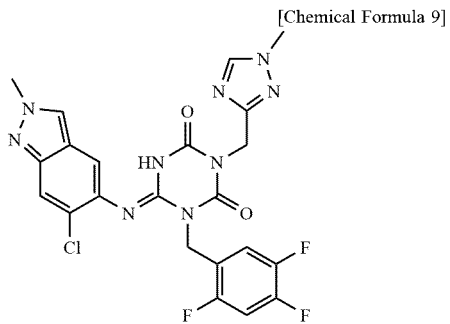

and fumaric acid are present in a molar ratio of 1 : 1.

(3B) A fumaric acid cocrystal according to the above item (1B) or (2B). (4B) The fumaric acid cocrystal Form I according to the above item (3B), which exhibits a powder X-ray diffraction pattern having peaks at diffraction angles (2θ): 9.5±0.2°, 10.9±0.2°, 18.6±0.2°, 23.5±0.2°, and 24.6±0.2°.

(5B) The fumaric acid cocrystal Form I according to the above item (3B), which exhibits a powder X-ray diffraction pattern having peaks at diffraction angles (2θ): 7.8±0.2°, 9.5±0.2°, 10.1±0.2°, 10.9±0.2°, 13.8±0.2°, 14.7±0.2°, 18.6±0.2°, 22.6±0.2°, 23.5±0.2°, and 24.6±0.2°.

(6B') The fumaric acid cocrystal Form I according to the above item (3B), which exhibits a Raman spectrum having Raman spectral peaks at 676.3 cm$^{-1}$±2 cm$^{-1}$, 748.0 cm$^{-1}$ ±2 cm$^{-1}$, 1029.3 cm$^{-1}$±2 cm$^{-1}$, 1374.4 cm$^{-1}$±2 cm$^{-1}$, 1515.5 cm$^{-1}$±2 cm$^{-1}$, 1665.7 cm$^{-1}$ ±2 cm$^{-1}$, 1715.7 cm$^{-1}$ ±2 cm$^{-1}$, and 1739.1 cm$^{-1}$±2 cm$^{-1}$.

(6B) A pharmaceutical composition comprising the cocrystal according to any one of the above items (3B) to (5B) and (6B').

(7B) The fumaric acid cocrystal Form I according to the above item (3B), whose crystallographic data when measured at 298 K is characterized by the following crystallographic data:
Space group: P-1
a = 8.4 Å±0.5 Å
b = 11.7 Å±0.5 Å
c = 15.2 Å±0.5 Å
α = 83.8°±0.5°
β = 78.9°±0.5°
γ = 77.1°±0.5°

(8B) The fumaric acid cocrystal Form I according to the above item (3B), whose crystallographic data when measured at 298 K is substantially in accordance with the following crystallographic data:
Space group: P-1
a = 8.4374 Å
b = 11.6780 Å
c = 15.1612 Å
α = 83.827°
β = 78.868°
γ = 77.147°

(9B) The fumaric acid cocrystal Form I according to the above item (3B), characterized by spectrum(spectra) and/or a curve selected from the following (a) to (c):
(a) a X ray powder diffraction spectrum substantially corresponding to FIG. 1;
(b) a Raman spectrum substantially corresponding to FIG. 3;
(c) a differential scanning calorimetry curve substantially corresponding to FIG. 4.

(10B) A pharmaceutical composition comprising the cocrystal according to any one of the above items (7B) to (9B).

Effect of the Invention

The compound of the present invention has inhibitory activity against coronavirus 3CL proteases and is useful as a therapeutic(treating) agent and/or prophylactic(preventing) agent for coronavirus infections. In addition, a pharmaceutical composition comprising a fumaric acid cocrystal of Compound (1-0115) is highly useful as a therapeutic agent for novel coronavirus infections (COVID-19).

BRIEF DESCRIPTION OF THE DRAWINGS

FIG. 1 shows a powder X-ray diffraction pattern of a fumaric acid cocrystal Form I (Form I) of the compound represented by Formula (I-B). The axis of abscissa represents 2θ(°), and the axis of ordinate represents the intensity (Count).

FIG. 2 shows a molecular structure in an asymmetric unit of the fumaric acid cocrystal Form I (Form I) of the compound represented by Formula (I-B).

FIG. 3 shows the Raman spectrum of the fumaric acid cocrystal Form I (Form I) of the compound represented by Formula (I-B). The axis of abscissa represents Raman shift (cm$^{-1}$), and the axis of ordinate represents the peak intensity.

FIG. 4 shows results of a DSC analysis of the fumaric acid cocrystal Form I (Form I) of the compound represented by Formula (I-B). The axis of abscissa represents temperature (°C), and the axis of ordinate represents the normalized heat flow (W/g).

FIG. 5 shows a powder X-ray diffraction pattern of a crystalline form of potassium salt Form I (Form I) of the compound represented by Formula (I-B). The axis of abscissa represents 2θ(°), and the axis of ordinate represents the intensity (Count).

FIG. 6 shows the Raman spectrum of the crystalline form of potassium salt Form I (Form I) of the compound represented by Formula (I-B). The axis of abscissa represents Raman shift (cm$^{-1}$), and the axis of ordinate represents the peak intensity.

FIG. 7 shows a powder X-ray diffraction pattern of a succinic acid cocrystal Form I (Form I) of the compound represented by Formula (I-B). The axis of abscissa represents 20(°), and the axis of ordinate represents the intensity (Count).

FIG. 8 shows the Raman spectrum of the succinic acid cocrystal Form I (Form I) of the compound represented by Formula (I-B). The axis of abscissa represents Raman shift (cm$^{-1}$), and the axis of ordinate represents the peak intensity.

FIG. 9 shows a powder X-ray diffraction pattern of a crystalline form of anhydride Form I (Form I) of the compound represented by Formula (I-B). The axis of abscissa represents 20(°), and the axis of ordinate represents the intensity (Count).

FIG. 10 shows the Raman spectrum of the crystalline form of anhydride Form I (Form I) of the compound represented by Formula (I-B). The axis of abscissa represents Raman shift (cm$^{-1}$), and the axis of ordinate represents the peak intensity.

FIG. 11 shows a powder X-ray diffraction pattern of a crystalline form of sodium salt Form I (Form 1) of the compound represented by Formula (I-B). The axis of abscissa represents 20(°), and the axis of ordinate represents the intensity (Count).

FIG. 12 shows the Raman spectrum of the crystalline form of sodium salt Form I (Form I)of the compound represented by Formula (I-B). The axis of abscissa represents Raman shift (cm$^{-1}$), and the axis of ordinate represents the peak intensity.

FIG. 13 shows results of a TG/DTA analysis of a crystalline form of sodium salt Form I (Form I) of the compound represented by Formula (I-B). The axis of ordinate represents the heat flow (μV)or the change in weight (%), and the axis of abscissa represents temperature (°C). Cel in the diagram means degree Celsius (°C).

MODE FOR CARRYING OUT THE INVENTION

Hereinafter, the meaning of each term used in the present specification will be described. Unless particularly stated otherwise, each term is used in the same sense, either alone or in combination with other terms.

The term "consist of" means having only the constituent elements.

The term "comprise" means that elements are not limited to the constituent elements, and elements that are not described are not excluded.

Hereinafter, the present invention will be described while showing exemplary embodiments. Throughout the present specification, it should be understood that, unless particularly stated otherwise, an expression of a singular form also includes the concept of a plural form thereof. Therefore, it should be understood that, unless particularly stated otherwise, an article for a singular form (for example, in the case of English, "a", "an", "the", or the like) also includes the concept of a plural form thereof.

Furthermore, it should be understood that, unless particularly stated otherwise, the terms used in the present specification are used in the meanings normally used in the above-described art. Accordingly, unless otherwise defined, all terminologies and scientific and technical terms used in the present specification have the same meanings as commonly understood by those having ordinary skill in the art to which the present invention belongs. In a case of contradiction, priority is given to the present specification (including definitions).

"Halogen" includes a fluorine atom, a chlorine atom, a bromine atom, and an iodine atom. Particularly, a fluorine atom and a chlorine atom are preferred.

"Alkyl" includes linear or branched hydrocarbon groups each having 1 to 15 carbon atoms, preferably 1 to 10 carbon atoms, more preferably 1 to 6 carbon atoms, and even more preferably 1 to 4 carbon atoms. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, and n-decyl.

Preferred embodiments of "alkyl" include methyl, ethyl, n-propyl, isopropyl, n-butyl, isobutyl, sec-butyl, tert-butyl, and n-pentyl. More preferred embodiments include methyl, ethyl, n-propyl, isopropyl, and tert-butyl.

"Aromatic carbocyclyl" means a cyclic aromatic hydrocarbon group having a single ring or two or more rings. Examples include phenyl, naphthyl, anthryl, and phenanthryl. Examples of 6-membered aromatic carbocyclyl include phenyl.

"Aromatic heterocyclyl" means an aromatic cyclyl having a single ring or two or more rings, which has one or more identical or different heteroatoms optionally selected from O, S, and N in the ring(s).

An aromatic heterocyclyl having two or more rings also includes an aromatic heterocyclyl having a single ring or two or more rings, to which a ring in the "aromatic carbocyclyl" is fused, and the linking bond may be carried by any of the rings.

The aromatic heterocyclyl having a single ring is preferably a 5- to 8-membered ring, and more preferably a 5-membered or 6-membered ring. Examples of 5-membered aromatic heterocyclyl include pyrrolyl, imidazolyl, pyrazolyl, triazolyl, tetrazolyl, furyl, thienyl, isoxazolyl, oxazolyl, oxadiazolyl, isothiazolyl, thiazolyl, and thiadiazolyl.

The aromatic heterocyclyl having two rings is preferably an 8- to 10-membered ring, and more preferably a 9-membered or 10-membered ring. Examples include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, and thiazolopyridyl. Examples of 9-membered aromatic heterocyclyl include indolyl, isoindolyl, indazolyl, indolizinyl, purinyl, benzimidazolyl, benzisoxazolyl, benzoxazolyl, benzoxadiazolyl, benzisothiazolyl, benzothiazolyl, benzothiadiazolyl, benzotriazolyl, benzofuranyl, imidazopyridyl, triazolopyridyl, oxazolopyridyl, and thiazolopyridyl.

Examples of the substituents of the "substituted or unsubstituted aromatic heterocyclyl" in R$^1$ include:

halogen; cyano; hydroxy;

substituted alkyl (Examples of the substituents include halogen, hydroxy, carbamoyl, aromatic carbocyclyl, non-aromatic carbocyclyl); unsubstituted alkyl;

unsubstituted alkyloxy, unsubstituted alkyloxycarbonyl;

unsubstituted aromatic carbocyclyl. It may be substituted with one or more group(s) selected from these.

Examples of the substituents of the "substituted or unsubstituted aromatic carbocyclyl" in R$^2$ include:

halogen; cyano;

substituted alkyl (Examples of the substituents include halogen); unsubstituted alkyl;

substituted alkyloxy (Examples of the substituents include halogen, aromatic carbocyclyl); unsubstituted alkyloxy. It may be substituted with one or more group(s) selected from these.

Examples of the substituents of the "substituted or unsubstituted aromatic heterocyclyl" in R$^3$ include:

halogen; hydroxy;

substituted alkyl (Examples of the substituents include halogen, hydroxy, alkyloxy, haloalkyloxy, alkylamino, alkylcarbonylamino, alkylcarbamoyl, alkylsulfonyl, non-aromatic carbocyclyl, non-aromatic heterocyclyl); unsubstituted alkyl. It may be substituted with one or more group(s) selected from these.

The compounds represented by Formula (I) is not limited to specific isomers, but include all possible isomers (eg, keto-enol isomer, imine- enamin isomers, diastereoisomers, optical isomers, rotational isomers, etc.), racemates or mixtures thereof. For example, the compound in Formula (I), wherein Y is N and X is NH includes the following tautomers.

[Chemical Formula 10]

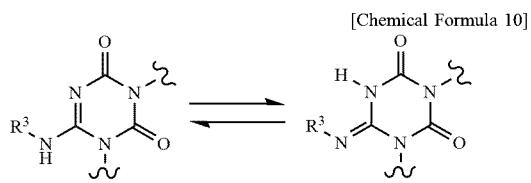

For example, Compound (1-0115) includes the following tautomers.

[Chemical Formula 11]

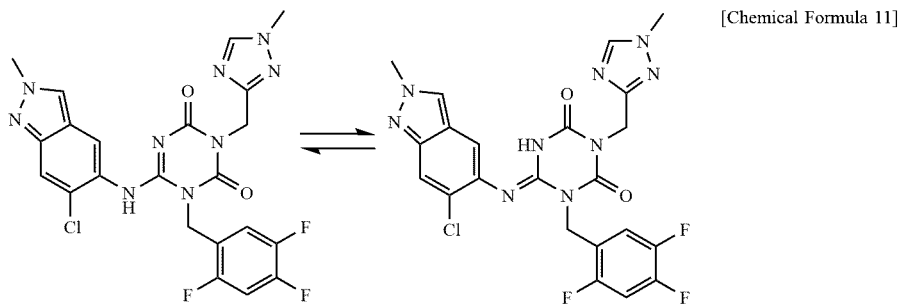

One or more hydrogen, carbon, and/or other atom(s) of the compounds represented by Formula (I) may be substituted by isotope(s) of hydrogen, carbon, and/or other atom(s), respectively. Examples of such isotopes include hydrogen, carbon, nitrogen, oxygen, phosphorus, sulfur, fluorine, iodine, and chlorine, as in the cases of $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{123}$I, and $^{36}$Cl, respectively. The compounds represented by Formula (I) also include compounds substituted with such isotopes. The compounds substituted with the isotopes are also useful as pharmaceutical products and include all radiolabeled forms of the compounds represented by Formula (I). Furthermore, a "radiolabeling method" for producing the "radiolabeled forms" is also included in the present invention, and the "radiolabeled forms" are useful as tools for metabolic pharmacokinetics studies, studies on binding assay, and/or diagnostics.

Furthermore, the crystalline form of the present invention may also be a deuterated form. The crystalline form of the present invention may also be labeled with radioisotopes (for example, $^3$H, $^{14}$C, $^{35}$S, and $^{125}$I).

Radiolabeled forms of the compounds represented by Formula (I) can be prepared by methods well known in the pertinent art. For example, a tritium-labeled compound represented by Formula (I) can be prepared by introducing tritium into a specific compound represented by Formula (I), by a catalytic dehalogenation reaction using tritium. This method includes causing precursors obtained by appropriately substituting compounds represented by Formula (I) with halogen, to react with tritium gas in the presence of an appropriate catalyst, for example, Pd/C and in the presence or absence of a base. Regarding other appropriate methods for preparing tritium-labeled compounds, "Isotopes in the Physical and Biomedical Sciences, Vol. 1, Labeled Compounds (Part A), Chapter 6 (1987)" can be referred to. A $^{14}$C-labeled compound can be prepared by using a raw material having $^{14}$C carbon.

Examples of pharmaceutically acceptable salts of the compounds represented by Formula (I) include salts of compounds represented by Formula (1) with alkali metals (for example, lithium, sodium, and potassium), alkaline earth metals (for example, calcium and barium), magnesium, transition metals (for example, zinc and iron), ammonia, organic bases (for example, trimethylamine, triethylamine, dicyclohexylamine, ethanolamine, diethanolamine, triethanolamine, meglumine, ethylenediamine, pyridine, picoline, and quinoline), and amino acids, or salts with inorganic acids (for example, hydrochloric acid, sulfuric acid, nitric acid, carbonic acid, hydrobromic acid, phosphoric acid, and hydroiodic acid) and organic acids (for example, formic acid, acetic acid, propionic acid, trifluoroacetic acid, citric acid, lactic acid, tartaric acid, oxalic acid, maleic acid, fumaric acid, succinic acid, mandelic acid, glutaric acid, malic acid, benzoic acid, phthalic acid, ascorbic acid, benzenesulfonic acid, p-toluenesulfonic acid, methanesulfonic acid, ethanesulfonic acid, and trifluoroacetic acid). These salts can be formed according to methods that are conventionally carried out.

The compounds represented by Formula (I) of the present invention or pharmaceutically acceptable salts thereof may form solvates (for example, hydrates), cocrystals, and/or crystalline polymorphs, and the present invention also includes such various solvates, cocrystals, and crystalline polymorphs. The "solvates" may have the compounds represented by Formula (I) coordinated with any number of solvent molecules (for example, water molecules). Furthermore, crystalline polymorphs may be formed by recrystallizing the compounds represented by Formula (I) or pharmaceutically acceptable salts thereof.

"Crystal" as used in the present specification means a solid in which constituent atoms, ions, molecules, and the like are three-dimensionally arranged with regularity, and is distinguished from an amorphous solid that does not have such a regular internal structure. The crystal of the present invention may be a single crystal, a twin crystal, a polycrystal, or the like.

Furthermore, the "crystal" may include "crystalline polymorphs" that have the same composition but different arrangements in the crystal, and crystals including those crystalline polymorphs are referred to as "crystalline forms".

In addition, the compounds represented by Formula (I) may be converted to pharmaceutically acceptable salts thereof or pharmaceutically acceptable solvates of these compounds and salts. The crystal of the present invention may be any of these salts, hydrates, solvates, and crystalline polymorphs, and even mixtures of two or more are intended to be included in the scope of the invention.

The crystalline form and the crystallinity can be measured by numerous technologies including, for example, powder X-ray diffraction measurement, Raman spectroscopy, infrared absorption spectrometry, water absorption and desorption measurement, differential scanning calorimetry, and dissolution characteristics.

"Cocrystal" as used in the present specification means that, for example, a compound represented by Formula (I-B) and a counter molecule are regularly arranged in the same crystal lattice, and may include any number of counter molecules. Furthermore, cocrystal implies that an intermolecular interaction between a compound and a counter molecule involves non-covalent and non-ionic chemical interaction such as hydrogen bonding and van der Waals force. A cocrystal is distinguished from a salt from the viewpoint that the compound is essentially uncharged or neutral. The cocrystal is distinguished from hydrate or solvate from the viewpoint that the counter molecule is neither water nor a solvent.

A complex comprising the compound represented by Formula (I-B) of the present invention includes, in a broad sense, a salt, a co-crystal and a clathrate compound, or a solvate thereof.

The "solvate" as used in the present specification means that, for example, with regard to the compounds represented by Formula (I) and Formula (I-B), the compounds and any number of solvent molecules are arranged with regularity.

Examples of the solvent molecules include acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methyl butyl ketone, methylcyclohexane, N-methylpyrrolidone, nitromethane, pyridine, sulfolane, tetralin, toluene, 1,1,2-trichloroethene, xylene, acetic acid, anisole, 1-butanol, 2-butanol, n-butyl acetate, t-butyl methyl ether, cumene, dimethyl sulfoxide, ethyl acetate, diethyl ether, ethyl formate, formic acid, heptane, isobutyl acetate, isopropyl acetate, methyl acetate, 3-methyl-1-butanol, methyl ethyl ketone, methyl isobutyl ketone, 2-methyl-1-propanol, pentane, 1-pentanol, 1-propanol, 2-propanol, propyl acetate, tetrahydrofuran, water (that is, hydrate), ethanol, acetone, 1,1-diethoxypropane, 1,1-dimethoxymethane, 2,2-dimethoxypropane, isooctane, isopropyl ether, methyl isopropyl ketone, methyltetrahydrofuran, petroleum ether, trichloroacetic acid, and trifluoroacetic acid; preferably acetic acid, anisole, 1-butanol, 2-butanol, n-butyl acetate, t-butyl methyl ether, cumene, dimethyl sulfoxide, ethyl acetate, diethyl ether, ethyl formate, formic acid, heptane, isobutyl acetate, isopropyl acetate, methyl acetate, 3-methyl-1-butanol, methyl ethyl ketone, methyl isobutyl ketone, 2-methyl-l-propanol, pentane, 1-pentanol, 1-propanol, 2-propanol, propyl acetate, tetrahydrofuran, water (that is, hydrate), ethanol, acetone, 1,1-diethoxypropane, 1,1-dimethoxymethane, 2,2-dimethoxypropane, isooctane, isopropyl ether, methyl isopropyl ketone, methyltetrahydrofuran, petroleum ether, trichloroacetic acid, and more preferably water (that is, hydrate), ethanol, acetone, 1,1-diethoxypropane, 1,1-dimethoxymethane, 2,2-dimethoxypropane, isooctane, isopropyl ether, methyl isopropyl ketone, methyltetrahydrofuran, petroleum ether, trichloroacetic acid, and trifluoroacetic acid.

Furthermore, the compounds represented by Formula (I), or pharmaceutically acceptable salts, cocrystals, and complexes of the compounds absorb moisture by being left to stand in atmosphere and may have water of adsorption attached thereto or may form hydrates.

The compounds represented by Formula (I) of the present invention or pharmaceutically acceptable salts thereof may form prodrugs, and the present invention also includes such various prodrugs. A prodrug is a derivative of a compound of the present invention having a group that can be chemically or metabolically degraded, and is a compound which becomes a pharmaceutically active compound of the present invention in vivo as a result of solvolysis or under physiological conditions. Prodrugs include compounds that are subjected to enzymatic oxidation, reduction, hydrolysis, and the like under physiological conditions in the living body and are converted to the compounds represented by Formula (I); compounds that are hydrolyzed by gastric acid or the like and are converted to the compounds represented by Formula (I); and the like. Methods for selecting and producing an appropriate prodrug derivative are described in, for example, "Design of Prodrugs, Elsevier, Amsterdam, 1985". A prodrug may have activity per se.

Powder X-Ray Diffraction (XRPD)

Powder X-ray diffraction (XRPD) is one of the most highly sensitive analysis methods for measuring the crystalline form and crystallinity of a solid. When X-rays are irradiated on a crystal, the rays are reflected at crystal lattice planes, interfere with each other, and show well-ordered diffraction lines corresponding to the period of the structure. On the other hand, in an amorphous solid, a diffraction phenomenon does not occur because an amorphous solid usually does not have a well-ordered repetitive period in the structure, and an uncharacterized broad XRPD pattern (also called halo pattern) is exhibited.

The crystalline forms of the compound represented by Formula (I-B) are discernable by powder X-ray diffraction patterns and characteristic diffraction peaks. The crystalline forms of the compound represented by Formula (I-B) can be distinguished from other crystalline forms by the presence of characteristic diffraction peaks.

Characteristic diffraction peaks used in the present specification are peaks selected from an observed diffraction pattern. Characteristic diffraction peaks are preferably selected from about 10 peaks, more preferably about 5 peaks, and even more preferably about 3 peaks, in a diffraction pattern.

When distinguishing a plurality of crystals, a peak that is identified in the relevant crystal and is not identified in other crystals becomes a characteristic peak preferable for characterizing the crystal, rather than the intensity of a peak. With such characteristic peaks, even one or two peaks can characterize the crystal. When the charts obtained by measurement are compared and these characteristic peaks are found to coincide, it can be said that the powder X-ray diffraction patterns substantially coincide.

Generally, since the diffraction angle (2θ) in powder X-ray diffraction may cause an error within the range of ±0.2°, it should be understood that a value of the diffraction angle of powder X-ray diffraction also includes numerical values within the range of about ±0.2°. Therefore, not only crystals in which the diffraction angles of peaks in powder X-ray diffraction perfectly coincide, but also crystals in which the diffraction angles of peaks coincide with an error of about ±0.2°, are included in the present invention.

It is known that generally, the intensity of a peak indicated in the following tables and drawings may fluctuate due to many factors, for example, the effect of selective orientation of crystals with respect to an X-ray beam, the influence of coarse particles, the purity of the substance to be analyzed, or the crystallinity of a sample. Furthermore, the peak position can also be shifted based on the fluctuation of the sample height. In addition, when the peak position is measured using different wavelengths, different shifts can be obtained according to Bragg equation (nλ=2dsinθ); however, other XRPD patterns obtainable by using such other wavelengths are also included in the scope of the present invention.

Single Crystal Structure Analysis

In one of the methods for characterizing a crystal, crystallographic parameters for the relevant crystal, as well as the atomic coordinates (values indicating the spatial positional relationship of each atom) and a three-dimensional structural model can be obtained. See "Guidance on X-ray Structural Analysis", written by Toshio Sakurai, published by Shokabo Co., Ltd. (1983); X-Ray Structure Determination: A Practical Guide, written by Stout & Jensen, Macmillan Co, New York (1968); and the like. When the crystal structures of a complex, a salt, an optical isomer, a tautomer, and a geometrical isomer such as the present invention are identified, single crystal structure analysis is useful.

Raman Spectroscopy

Raman spectroscopy shows the characteristics of the oscillation of a molecular or composite system. Its origin lies in the inelastic collision between molecules and photons, which are particles of light including light rays. Collision between molecules and photons results in the exchange of energy, which results in a change in energy, and thereby the wavelength of the photons changes. That is, since the Raman spectrum is a spectral line of very narrow wavelengths, which is emitted when photons are incident on a molecule of interest, lasers and the like are used as light sources. The wavelength of each Raman line is indicated by the wavenumber shift from incident light, and this is the difference between the Raman line and the reciprocal of the wavelength of incident light. Raman spectroscopy is to measure the state of oscillation of molecules, and this is determined by the molecular structure thereof.

Generally, since Raman spectral peaks (cm$^{-1}$) can cause errors within the range of ±2 cm$^{-1}$, it should be understood that the values of the above-described Raman spectral peaks also include numerical values within the range of about ±2 cm$^{-1}$. Therefore, not only the crystals whose Raman spectral peaks in the Raman spectra perfectly coincide, but also the crystals whose Raman spectral peaks coincide with errors of about ±2 cm$^{-1}$, are included in the present invention.

Differential Scanning Calorimetry (DSC)

DSC is one of important measurement methods for thermal analysis and is a method of measuring the thermal properties of a substance as an aggregate of atoms and molecules.

A differential scanning calorimetric curve is obtained by measuring the temperature-related or time-related change in the calorific value of a pharmaceutically active ingredient by DSC and plotting the obtained data with respect to temperature or time. From the differential scanning calorimetric curve, information on the onset temperature at the time of melting of the pharmaceutically active ingredient, the maximum value of the endothermic peak curve associated with melting, and the enthalpy can be obtained.

With regard to DSC, it is known that the temperature to be observed may depend on the rate of temperature change as well as the sample preparation technique and the particular apparatus used. Therefore, the "melting point" in DSC refers to the onset temperature that is not likely to be affected by the sample preparation technique. The error range for the onset temperature obtainable from the differential scanning calorimetry curve is approximately ±2° C. For the recognition of identity of crystals, not only the melting point but also the overall pattern are important, and there may be some variation depending on the measurement conditions and the measuring equipment.

Simultaneous Differential Thermal Analysis and Thermogravimetric Analysis (TG/DTA)

TG/DTA is one of important measurement methods for thermal analysis and is a method of measuring the weight and thermal properties of a substance as an aggregate of atoms and molecules.

TG/DTA is a method of measuring the temperature-related or time-related changes in weight and calorific value of a pharmaceutically active ingredient, and a TG (thermogravimetric) and DTA (differential thermal) curve is obtained by plotting obtained data with respect to temperature or time. From the TG/DTA curve, information on the changes in weight and calorific value in relation to degradation, dehydration, oxidation, reduction, sublimation, and evaporation of a pharmaceutically active ingredient can be obtained.

With regard to TG/DTA, it is known that the temperature to be observed and the weight change may depend on the rate of temperature change as well as the sample preparation technique and the particular apparatus used. Therefore, the "melting point" in TG/DTA refers to the onset temperature that is not likely to be affected by the sample preparation technique. For the recognition of identity of crystals, not only the melting point but also the overall pattern are important, and there may be some variation depending on the measurement conditions and the measuring equipment.

Since the compound according to the present invention has coronavirus 3CL protease inhibitory activity, the compound is useful as a therapeutic and/or prophylactic agent for a disease associated with coronavirus 3CL proteases. When the term "therapeutic agent and/or prophylactic agent" is used in the present invention, this also includes a symptom ameliorating agent. The disease associated with coronavirus 3CL proteases may be viral infections, and preferably coronavirus infections.

According to an aspect, the coronavirus may be a coronavirus that infects human beings. The coronavirus that infects human beings may be HCoV-229E, HCoV-NL63, HCoV-HKU1, HCoV-OC43, SARS-CoV, MERS-CoV, and/or SARS-CoV-2.

According to an aspect, the coronavirus may be alphacoronavirus and/or betacoronavirus, and more preferably betacoronavirus.

According to an aspect, the alphacoronavirus may be HCoV-229E and HCoV-NL63. The alphacoronavirus may be particularly preferably HCoV-229E.

According to an aspect, the betacoronavirus may be HCoV-HKU1, HCoV-OC43, SARS-CoV, MERS-CoV, and/or SARS-CoV-2. The betacoronavirus may be HCoV-OC43 or SARS-CoV-2, and particularly preferably SARS-CoV-2.

According to an aspect, the betacoronavirus may be betacoronavirus lineage A (δ-coronavirus lineage A), betacoronavirus lineage B (δ-coronavirus lineage B), and betacoronavirus lineage C ß-coronavirus lineage C). The betacoronavirus may be more preferably betacoronavirus lineage A (δ-coronavirus lineage A) and betacoronavirus lineage B (δ-coronavirus lineage B) and particularly preferably betacoronavirus lineage B (δ-coronavirus lineage B).

According to an aspect, the betacoronavirus may be a betacoronavirus of the subgenus Sarbecovirus.

Examples of the betacoronavirus lineage A (δ-coronavirus lineage A) include HCoV-HKU1 and HCoV-OC43, and preferably HCoV-OC43. Examples of the betacoronavirus lineage B (δ-coronavirus lineage B) include SARS-CoV and SARS-CoV-2, and preferably SARS-CoV-2. The betacoronavirus lineage C (δ-coronavirus lineage C) may be MERS-CoV.

According to an aspect, the coronavirus may be HCoV-229E, HCoV-OC43, and/or SARS-CoV-2, and particularly preferably SARS-CoV-2.

The coronavirus infections may be infections caused by HCoV-229E, HCoV-NL63, HCoV-OC43, HCoV-HKU1, SARS-CoV, MERS-CoV, and/or SARS-CoV-2. Preferably, the coronavirus infections may be infections caused by HCoV-229E, HCoV-OC43, and/or SARS-CoV-2, and particularly preferably infection caused by SARS-CoV-2.

The coronavirus infections may be particularly preferably novel coronavirus infections (COVID-19).

Method for Producing Compound of Present Invention

The compounds represented by Formula (I) according to the present invention can be produced by, for example, the general synthesis method described below. Regarding extraction, purification, and the like, the treatments carried out in ordinary experiments of organic chemistry may be carried out. The compounds of the present invention can be produced with reference to techniques known in the art. For example, the compounds can be produced with reference to WO2010092966, WO2012020749, WO2013089212, WO2014200078, WO2012020742, and WO2013118855.

(Method A) When Y is N, and X is $NR^6$ or O

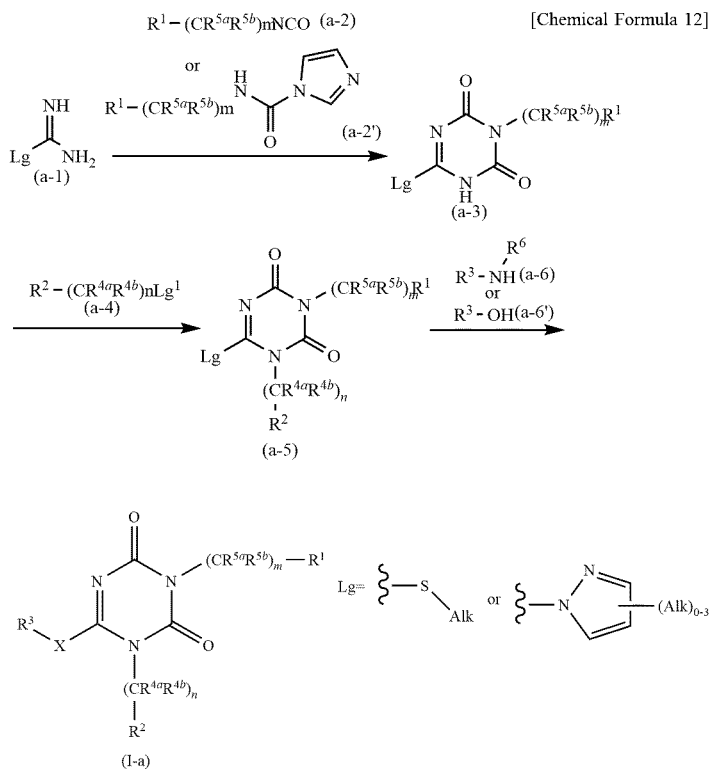

[Chemical Formula 12]

wherein Alk is C1-C3 alkyl; $Lg^1$ is a leaving group; and reference symbols other than those have the same meanings as described above.

First Step

Compound (a-1), or hydrochloride or bromate thereof is reacted with isocyanate (a-2) or 1-carbamoylimidazole (a-2') in a solvent such as N,N-dimethylformamide, N,N-dimethylacetamide, N,N'-dimethylimidazolidinone, dimethyl sulfoxide, or THF, in the presence of a base such as DBU, triethylamine, N,N-diisopropylethylamine, or pyridine (preferably, DBU), at -20° C. to 50° C., and preferably -10° C. to a condition under ice cooling. Subsequently, Compound (a-3) can be produced by reacting the reaction mixture with a carbonylating agent such as 1,1'-carbonyldiimidazole, phosgene, or triphosgene, and a base such as DBU, triethylamine, N,N-diisopropylethylamine, or pyridine (preferably, DBU), at -20° C. to 50° C., and preferably -10° C. to a condition under ice cooling.

Second Step

Compound (a-5) can be produced by reacting Compound (a-3) with Compound (a-4) in a solvent such as acetonitrile, acetone, DMF, or DMSO, in the presence of a base such as potassium carbonate, sodium carbonate, or N,N-diisopropylethylamine, at 50° C. to a condition of heating under reflux, and preferably under a condition of heating under reflux.

Examples of the leaving group include halogen and —$OSO_2(C_tF_{2t+1})$, wherein t is an integer of 1 to 4. The halogen is preferably chlorine, iodine, and bromine, and the —OSO$_2$(C$_t$F$_{2t+1}$) group is preferably an —OTf group (trifluoromethanesulfonic acid ester).

Third Step

A compound represented by Compound (I-a) can be produced by reacting Compound (a-5) with Compound (a-6) or Compound (a-6') in a solvent such as NMP, DMF, DMA, DMSO, tert-butanol, or 2-methyl-2-butanol, in the presence or absence of an acid such as acetic acid, at 60° C. to 150° C., and preferably 80° C. to 120° C.

Since the compound of the present invention has coronavirus 3CL protease inhibitory activity, the compound is useful as a therapeutic and/or prophylactic agent for coronavirus infections.

Furthermore, the compound of the present invention has utility as a medicine, and preferably, the compound of the present invention has any one or a plurality of the following excellent features.

a) Inhibitory activity against CYP enzymes (for example, CYP1A2, CYP2C9, CYP2C19, CYP2D6, and CYP3A4) is weak.
b) Satisfactory pharmacokinetics such as high bioavailability and adequate clearance are exhibited.
c) Metabolic stability is high.
d) Irreversible inhibitory activity is not exhibited against CYP enzymes (for example, CYP3A4) within the concentration range of the measurement conditions described in the present specification.
e) Mutagenicity is not exhibited.
f) The cardiovascular risk is low.
g) High solubility is exhibited.
h) The protein unbinding rate (fu value) is high.
i) High coronavirus 3CL protease selectivity is exhibited.
j) High coronavirus replication inhibitory activity is exhibited. For example, high coronavirus replication inhibitory activity is exhibited when human blood serum (HS) or human serum albumin (HSA) is added.

Regarding the coronavirus replication inhibitor, for example, an aspect in which in the CPE effect (SARS-CoV-2) that will be described below, for example, EC$_{50}$ is 10 µM or less, preferably 1 µM or less, and more preferably 100 nM or less, may be mentioned.

Furthermore, a salt, a crystalline form, a composite, and a cocrystal of the compound according to the present invention have utility as medicines, and preferably, they have any one or a plurality of the following excellent features.

bb) Satisfactory pharmacokinetics such as high bioavailability, adequate clearance, high AUC, and high maximum blood concentration are exhibited.

gg) High solubility, high chemical stability, and low hygroscopic properties are exhibited.

The pharmaceutical composition of the present invention can be administered by either an oral method or a parenteral method. Examples of a parenteral administration method include percutaneous, subcutaneous, intravenous, intraarterial, intramuscular, intraperitoneal, transmucosal, inhalation, transnasal, ocular instillation, ear instillation, and intravaginal administration.

In the case of oral administration, the pharmaceutical composition may be prepared into any dosage form that is commonly used, such as a solid preparation for internal use (for example, a tablet, a powder preparation, a granular preparation, a capsule, a pill, or a film preparation), or a liquid preparation for internal use (for example, a suspension, an emulsion, an elixir, a syrup, a limonade, a spirit preparation, an aromatic water preparation, an extraction, a decoction, or a tincture) and administered. The tablet may be a dragee, a film-coated tablet, an enteric-coated tablet, a sustained release tablet, a troche, a sublingual tablet, a buccal tablet, a chewable tablet, or an orally disintegrating tablet; the powder preparation and granular preparation may be dry syrups; and the capsule may be a soft capsule, a microcapsule, or a sustained release capsule.

In the case of parenteral administration, the pharmaceutical composition can be suitably administered in any dosage form that is commonly used, such as an injectable preparation, an infusion, or a preparation for external use (for example, an eye drop, a nasal drop, an ear drop, an aerosol, an inhalant, a lotion, an impregnating agent, a liniment, a gargling agent, an enema, an ointment, a plaster, a jelly, a cream, a patch, a poultice, a powder preparation for external use, or a suppository). The injectable preparation may be an O/W, W/O, O/W/O, or W/O/W type emulsion, or the like.

A pharmaceutical composition can be obtained by mixing an effective amount of the compound of the present invention with various pharmaceutical additives appropriate for the dosage form, such as an excipient, a binder, a disintegrating agent, and a lubricating agent, as necessary. Furthermore, the pharmaceutical composition can be prepared into a pharmaceutical composition for use for a child, an elderly, a patient with a serious case, or a surgical operation, by appropriately changing the effective amount of the compound of the present invention, the dosage form, and/or various pharmaceutical additives. For example, a pharmaceutical composition for use for a child may be administered to a neonate (less than 4 weeks after birth), an infant (from 4 weeks after birth to less than 1 year), a preschool child (from 1 year to less than 7 years), a child (from 7 years to less than 15 years), or a patient 15 year to 18 years of age. For example, a pharmaceutical composition for an elderly may be administered to a patient 65 years of age or older.

It is desirable to set the amount of administration of the pharmaceutical composition of the present invention (for example, a pharmaceutical composition comprising a fumaric acid cocrystal Form I of a compound represented by Formula (I-B)), after considering the age and body weight of the patient, the type and degree of the disease, the route of administration, and the like; however, in the case of oral administration, the amount of administration is usually 0.05 to 200 mg/kg/day and is preferably in the range of 0.1 to 100 mg/kg/day. In the case of parenteral administration, the amount of administration may vary greatly depending on the route of administration; however, the amount of administration is usually 0.005 to 200 mg/kg/day and is preferably in the range of 0.01 to 100 mg/kg/day. This may be administered once a day or several times a day.

The compound of the present invention may be used in combination with, for example, another therapeutic agent for novel coronavirus infections (COVID-19) (the therapeutic agent includes an approved drug and a drug that is under development or to be developed in the future) (hereinafter, referred to as concomitant drug), for the purpose of enhancing the action of the compound, reducing the amount of administration of the compound, or the like. At this time, the timing of administration for the compound of the present invention and the concomitant drug is not limited, and these may be administered simultaneously to the target of administration or may be administered with a time difference. Furthermore, the compound of the present invention and the concomitant drug may be administered as two or more kinds of preparations each including active ingredients, or may be administered as a single preparation including those active ingredients.

The amount of administration of the concomitant drug can be appropriately selected based on the clinically used dosage. Furthermore, the blending ratio of the compound of the present invention and the concomitant drug can be appropriately selected according to the target of administration, the route of administration, the target disease, symptoms, combination, and the like. For example, when the target of administration is a human being, 0.01 to 100 parts by weight of the concomitant drug may be used with respect to 1 part by weight of the compound of the present invention.

EXAMPLES

Hereinafter, the present invention will be described in more detail by way of Examples, Reference Examples, and Test Examples; however, the present invention is not intended to be limited by these.

Furthermore, abbreviations used in the present specification denote the following meanings.

Boc: tert-butoxycarbonyl
DBU: 1,8-Diazabicyclo[5.4.0]-7-undecene
DMA: N,N-dimethylacetamide
DMF: N,N-dimethylformamide
DMSO: Dimethyl sulfoxide
DTT: Dithiothreitol
EDC: 1-Ethyl-3-(3-dimethylaminopropyl)carbodiimide
EDT: 1,2-Ethanedithiol
EDTA: Ethylenediaminetetraacetic acid
FBS: Fetal bovine serum
HOBT: 1-Hydroxybenzotriazole
LHMDS: Lithium bis(trimethylsilyl)amide
MEM: Eagle's Minimum Essential Medium
NMP: N-methylpyrrolidone
TFA: Trifluoroacetic acid
THF: Tetrahydrofuran
mM: mmol/L
μM: μmol/L
nM: nmol/L Method for Identifying Compound The NMR analysis obtained in each Example was performed at 400 MHz, and measurement was made using DMSO-$d_6$ and CDCl$_3$. Furthermore, when NMR data are shown, there are occasions in which all the measured peaks are not described.

The term RT in the specification indicates retention time in an LC/MS: liquid chromatography / mass analysis, and the retention time was measured under the following conditions.

Measurement Conditions 1

Column: ACQUITY UPLC (registered trademark) BEH C18 (1.7 μm i.d. 2.1 × 50 mm) (Waters)
Flow rate: 0.8 mL/min
UV detection wavelength: 254 nm
Mobile phase: [A] was 0.1% formic acid-containing aqueous solution, and [B] was 0.1% formic acid-containing acetonitrile solution.
Gradient: A linear gradient of 5% to 100% solvent [B] was carried out for 3.5 minutes, and then 100% solvent [B] was maintained for 0.5 minutes.

Incidentally, in the specification, the description of MS(m/z) indicates a value observed by mass analysis.

Measurement of Powder X-Ray Diffraction Pattern

Powder X-ray diffraction measurement of crystals obtained in each Example was performed according to the powder X-ray diffraction measurement method described in the General Testing Methods of the Japanese Pharmacopoeia. Measurement conditions are shown below.

Apparatus

SmartLab manufactured by Rigaku Corporation

Operation Method

Measurement method: Reflection method
Wavelength used: CuKa radiation
Tube current: 200 mA
Tube voltage: 45 kV
Sample plate: Aluminum
Incident angle of X-rays: 2.5°
Sampling width: 0.02°
Detector: HyPix-3000 (two-dimensional detection mode)

Measurement and Analysis Method for Single Crystal Structure Analysis

The measurement conditions and analysis method for single crystal structure analysis will be described below.

Apparatus

XtaLAB P200 MM007 manufactured by Rigaku Corporation

Measurement Conditions

Measurement temperature: 25° C.
Wavelength used: CuKa radiation ($\lambda$ = 1.5418Å)
Software: CrysAlisPro 1.171.39.46e (Rigaku Oxford Diffraction, 2018)
(Data processing)
Software: CrysAlisPro 1.171.39.46e (Rigaku Oxford Diffraction, 2018)
The data were subjected to Lorentz and polarization correction and absorption correction.

Crystal Structure Analysis

Phase determination was performed using a direct method program, ShelXT (Sheldrick, G.M., 2015), and regarding refinement, a full-matrix least squares method was carried out using ShelXL (Sheldrick, G.M., 2015). The temperature factors of non-hydrogen atoms were all subjected to refinement with anisotropy. Hydrogen atoms were computationally introduced using the default parameters of ShelXL and were treated as riding atoms. All the hydrogen atoms were subjected to refinement with isotropic parameters.

For the construction of FIG. 2 and FIG. 4, PLUTON (Spek, 1991)/ORTEP (Johnson, 1976) was used.

Measurement of Raman Spectrum

Measurement of the Raman spectrum of crystals obtained in each Example was performed. Measurement conditions are shown below.

Measuring instrument: RAMANTouch Vis2-NIR-SNU (manufactured by Nanophoton Corporation)
Measurement method: Microscopic laser Raman spectrometry
Laser wavelength: 671 nm
Diffraction grating: 600 grooves/mm
Detector: CCD detector
Object lens: 50 × (NA 0.80)
Cumulative number: 3 to 10 times
Exposure time: 1 to 10 seconds

Measurement of Differential Scanning Calorimetry (DSC)

About 3 mg of a sample obtained in each Example was weighed into an aluminum crimped pan, and DSC measurement was performed. Measurement conditions are shown below. Incidentally, in the measurement made by differential scanning calorimetry (DSC), an error can occur in the range of ±2° C.
Apparatus: TA Instrument Q1000/TA Instrument
Measurement temperature range: 0° C. to 295° C.
Rate of temperature increase: 10° C./min
Atmosphere: N₂ 50 mL/min

Measurement of TG/DTA Data

About 3 mg of the crystals obtained in each Example were weighed and packed into an aluminum pan, and measurement was performed in an open system. Measurement conditions are as follows.

Measurement Conditions 1

Apparatus: Hitachi High-Technologies TG/DTA STA7200RV
Measurement temperature range: Room temperature to 400° C.
Rate of temperature increase: 10° C./min

Example 1

Synthesis of Compound (I-0115)

Step 1 Synthesis of Compound 18

Compound 4 (926 mg, 4.04 mmol), acetonitrile (7.41 mL), potassium carbonate (726 mg, 5.25 mmol) and 2,4,5-trifluorobenzyl bromide (1000 mg, 4.44 mmol) were mixed. The reaction solution was stirred at 80° C. for 40 minutes, allowed to cool, and then diluted with ethyl acetate. After filtration of the insoluble material, the filtrate was concentrated to give the crude product of Compound 18 (1.51 g, 4.04 mmol, yield : quant.) LC/MS (ESI):m/z=374, RT=2.54 min, LC/MS measured condition 1

Step 2 Synthesis of Compound 19

Compound 18 (1.51 g, 4.04 mmol) and TFA (3.02 mL) were mixed. The reaction solution was stirred at room temperature for 4 hours and allowed to stand overnight. TFA was distilled off under reduced pressure, and then toluene was added to the residue and azeotroped. Isopropyl Ether was added to the residue, suspended, and collected by filtration to give Compound 19 (1.22 g, 3.84 mmol, yield : 95%)

LC/MS(ESI):m/z=318, RT=1.68min, LC/MS measured condition 1

Step 3 Synthesis of Compound 20

Compound 19 (200 mg, 0.63 mmol), DMF (1.8 mL), Potassium Carbonate (261 mg, 1.89 mmol) and 3-(chloromethyl)-1-methyl-1H-1,2,4-triazole hydrochloride (159 mg, 0.946 mmol) were mixed. The reaction solution was stirred

[Chemical Formula 13]

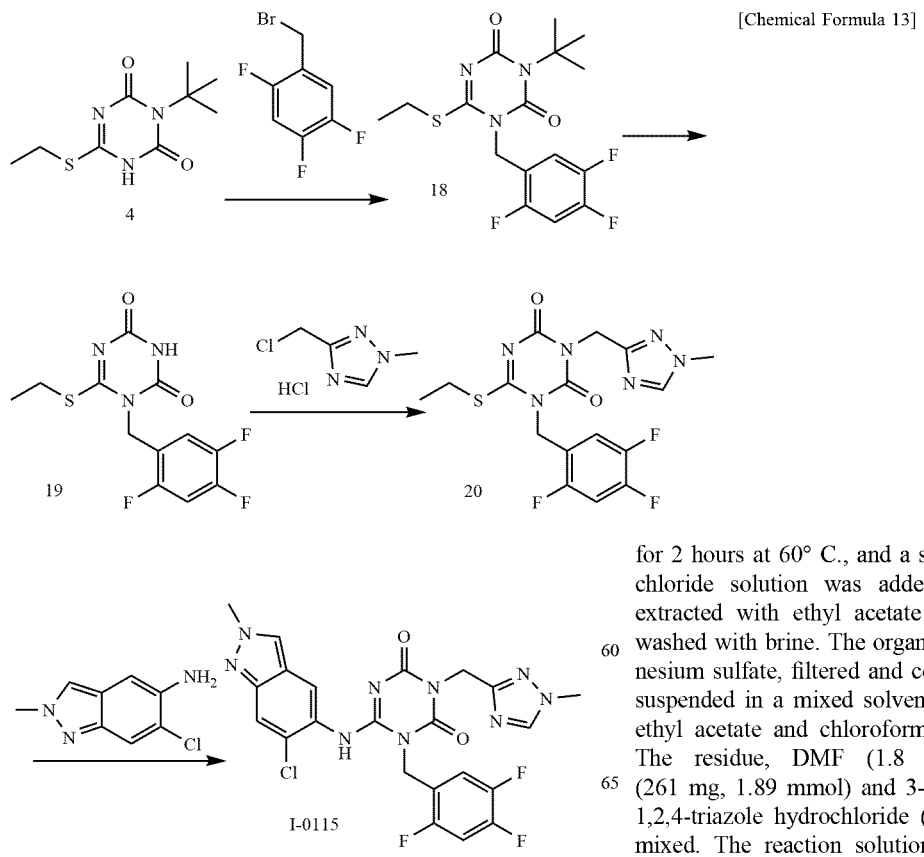

for 2 hours at 60° C., and a saturated aqueous ammonium chloride solution was added. The aqueous layer was extracted with ethyl acetate and the organic layer was washed with brine. The organic layer was dried over magnesium sulfate, filtered and concentrated. The residue was suspended in a mixed solvent of isopropyl ether, hexane, ethyl acetate and chloroform and collected by filtration. The residue, DMF (1.8 mL), potassium carbonate (261 mg, 1.89 mmol) and 3-(chloromethyl)-1-methyl-1H-1,2,4-triazole hydrochloride (159 mg, 0.946 mmol) were mixed. The reaction solution was stirred at 60° C. for 6 hours, and a saturated aqueous ammonium chloride solution was added. The aqueous layer was extracted with ethyl acetate and the organic layer was washed with brine. The organic layer was dried over magnesium sulfate, filtered and concentrated. The residue was suspended in a mixed solvent of isopropyl ether, hexane, ethyl acetate and chloroform and collected by filtration to give Compound 20 (116 mg, 0.281 mmol, 45% yield)

LC/MS(ESI): m/z = 413, RT=1.84min, LC/MS measured condition 1

Step 4 Synthesis of Compound (I-0115)

Compound 20 (115 mg, 0.279 mmol), THF (2.30 mL) and 6-chloro-2-methyl-2H-indazole-5-amine (60.8 mg, 0.335 mmol) were mixed. The reaction mixture was added dropwise LHMDS (558 µM, 0.558 mmol) at 0° C. The reaction mixture was stirred at 0° C. for 2.5 hours and stirred at room temperature for 40 minutes, then saturated ammonium chloride solution was added to the reaction mixture. The reaction mixture was extracted with chloroform and the organic layer was concentrated. The residue was purified by silicagel column chromatography (chloroform/methanol) to give Compound (I-0115) (61.8 mg, 0.116 mmol, Yield 42%).

$^1$H-NMR(CDCl$_3$)δ:7.96 (s, 1H), 7.82 (d, J = 2.5 Hz, 2H), 7.48 (br s, 1H), 7.45-7.37 (m, 1H), 7.08 (s, 1H), 6.97-6.88 (m, 1H), 5.35 (s, 2H), 5.17 (s, 2H), 4.21 (s, 3H), 3.89 (s, 3H).

LC/MS(ESI): m/z = 532, RT=1.70 min, LC/MS measurement method 1

The following compounds were synthesized according to the above general synthesis method and the method described in Examples. The structure and physical properties (LC / MS data) are shown in the table below.

The compound described by the amino structure:

[Chemical Formula 14]

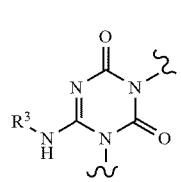

in the table, in which Y is N and X is NH in Formula (I), may have an imino structure:

[Chemical Formula 15]

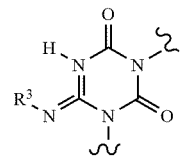

and the compound represented by the imino structure also may have the amino structure.

That is, even with the same compound, there are cases where it has an imino structure or an amino structure, depending on crystallization conditions and the like. Even with forming its salt or complex, the salt or the complex may have an amino structure or an imino structure. Even with the same counter molecule of the salt or the complex, they may have an amino structure or an imino structure depending on crystallization conditions and the like. It may also be the mixture of a compound having an imino structure, its salt or a complex thereof, and a compound having an amino structure, its salt or a complex thereof.

TABLE 1

| Compound No. | Structure | LC/MS Measured condition | Retention Time (min) | m/z | Configuration |
| --- | --- | --- | --- | --- | --- |
| I-0115 | 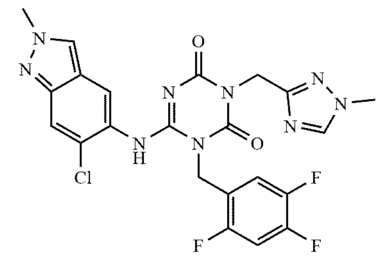 | 1 | 1.70 | 532 | |

Example 2

To Compound (I-0115, 1170 mg) were added fumaric acid (278 mg, 1.1 eq) and ethyl acetate(5.85 mL). The mixture was stirred at room temperature for 45 minutes. The resulting solids were collected by filtration and dried to give fumaric acid cocrystal Form I of the compound represented by Formula (I-B) (1369.4 mg, 94.6%).

The results of the single crystal structure analysis of the fumaric acid cocrystal Form I of the compound represented by the Formula (I-B) are shown below.

R1 (I> 2.00 s (I)) was 0.0470, and it was confirmed from the final difference Fourier that there was no lack of electron density or misplacement.

Crystallographic data are shown in Table 2.

TABLE 2

| Space Group | P-1 |
| --- | --- |
| a (Å) | 8.4374(2) |
| b (Å) | 11.6780(3) |
| c (Å) | 15.1612(4) |
| α (°) | 83.827(2) |
| δ (°) | 78.868(2) |
| γ (°) | 77.147(2) |
| Volume (Å$^3$) | 1425.77(6) |
| Z | 2 |
| Density (calculated value) (g/cm$^3$) | 1.509 |
| Measured temperature(K) | 298 |

Wherein Volume indicates the unit lattice volume, Z indicates chemical unit number per unit cell.

In addition, the atomic coordinates of non-hydrogen atoms are indicated in Tables 3 to 4. Here, U(eq) means an equivalent isotropic temperature factor.

TABLE 3

| Atom | x | y | z | U(eq) |
|---|---|---|---|---|
| Cl36 | 8115.3(9) | 8341.6(8) | 5010.7(5) | 79.9(3) |
| F32 | 8958.5(19) | 7981.3(17) | 307.5(9) | 78.5(5) |
| O35 | 7267(2) | 5961.4(16) | 1399.9(10) | 56.3(5) |
| O34 | 5322(3) | 4254.8(16) | 4098.2(11) | 63.3(5) |
| O38 | 3536(2) | 9367.5(19) | 8936.3(12) | 64.2(5) |
| N12 | 6506(2) | 7056.8(18) | 2611.0(12) | 44.2(5) |
| F33 | 13870(2) | 7642(2) | 1402.1(13) | 100.3(7) |
| N16 | 5475(2) | 6174.4(18) | 3988.1(12) | 48.2(5) |
| N14 | 6120(3) | 5115.3(18) | 2713.0(12) | 47.3(5) |
| N9 | 2815(3) | 8924(2) | 7397.8(13) | 55.4(6) |
| N10 | 5772(3) | 8146(2) | 3856.1(13) | 55.1(6) |
| N1 | 1276(3) | 8864(2) | 7324.6(14) | 60.2(6) |
| F31 | 12197(3) | 7751(3) | 3084.6(13) | 124.9(9) |
| N23 | 3644(3) | 4434(2) | 1818.7(15) | 64.5(6) |
| N20 | 3122(3) | 4249(2) | 1061.4(15) | 64.9(6) |
| C11 | 6673(3) | 6043(2) | 2193.8(15) | 44.7(6) |
| C9 | 5879(3) | 7178(2) | 3527.6(15) | 44.2(6) |
| C10 | 5619(3) | 5119(2) | 3639.3(15) | 48.4(6) |
| N22 | 5784(3) | 3621(2) | 814.1(15) | 67.8(7) |
| O39 | 6151(3) | 8893(3) | 8285.8(15) | 109.2(10) |
| C12 | 6985(3) | 8068(2) | 2049.4(15) | 47.2(6) |
| C20 | 5248(3) | 4044(2) | 1633.9(16) | 50.7(6) |
| C7 | 5022(3) | 8298(2) | 4770.9(15) | 50.8(6) |
| C4 | 3693(3) | 8762(2) | 6554.3(16) | 49.4(6) |
| C13 | 8823(3) | 7976(2) | 1872.6(16) | 48.8(6) |
| C5 | 5385(3) | 8700(2) | 6267.8(17) | 56.4(7) |
| C19 | 6380(3) | 4009(2) | 2279.5(17) | 54.5(7) |
| C14 | 9741(3) | 7934(2) | 1013.2(16) | 54.7(7) |
| C3 | 2685(3) | 8593(2) | 5965.2(17) | 54.4(7) |
| C6 | 6015(3) | 8469(2) | 5392.0(16) | 54.3(7) |
| C23 | 5121(4) | 9287(3) | 8898.3(18) | 62.1(7) |
| O41 | 1842(3) | 4874(3) | 3529.1(18) | 119.8(10) |
| C8 | 3370(3) | 8376(2) | 5054.8(17) | 57.4(7) |
| C24 | 5542(3) | 9730(3) | 9679.7(17) | 61.9(7) |
| C18 | 9684(4) | 7917(3) | 2570.7(18) | 67.1(8) |
| C15 | 11431(3) | 7827(3) | 831.3(19) | 67.8(8) |
| C16 | 12217(3) | 7760(3) | 1541(2) | 67.9(8) |
| C2 | 1134(4) | 8667(3) | 6497.1(18) | 67.4(8) |

TABLE 4

| Atom | x | y | z | U(eq) |
|---|---|---|---|---|
| C17 | 11360(4) | 7806(3) | 2405(2) | 75.0(9) |
| C21 | 4400(4) | 3767(3) | 485.7(19) | 70.6(8) |
| O43 | -464(4) | 4618(4) | 3203.2(19) | 154.2(15) |
| C1 | 9(4) | 8943(3) | 8139(2) | 81.7(10) |
| C26 | 307(4) | 4766(4) | 3745(2) | 93.6(12) |
| C25 | -384(4) | 4909(4) | 4700(2) | 92.1(11) |
| C22 | 1397(4) | 4562(4) | 963(3) | 102.7(13) |

Next, the atomic coordinates of the hydrogen atom are shown in Table 5. Here, U(iso) means an isotropic temperature factor. In addition, the numbers of hydrogen atoms in Table 5 are assigned in relation to the numbers of non-hydrogen atoms that are bonded.

TABLE 5

| Atom | x | y | z | U(iso) |
|---|---|---|---|---|
| H38 | 3370.9 | 9206.88 | 8452.86 | 96 |
| H16 | 5092.25 | 6215.55 | 4554.71 | 58 |
| H12A | 6452.59 | 8783.45 | 2347.49 | 57 |
| H12B | 6603.63 | 8119.01 | 1479.7 | 57 |
| H5 | 6053.99 | 8811.71 | 6658.45 | 68 |
| H19A | 6229.72 | 3381.57 | 2741.61 | 65 |
| H19B | 7509.94 | 3824.57 | 1962.58 | 65 |
| H41 | 2202.36 | 4700.41 | 3007.94 | 180 |
| H8 | 2702.01 | 8287.11 | 4656.27 | 69 |
| H24 | 6652.83 | 9619.42 | 9719.44 | 74 |
| H18 | 9115.24 | 7953.15 | 3160.4 | 81 |
| H15 | 12010.7 | 7800.84 | 243.55 | 81 |
| H2 | 176.44 | 8593.16 | 6310.6 | 81 |
| H21 | 4344.44 | 3553.57 | -79.51 | 85 |
| H1A | 260.69 | 8258.79 | 8539.89 | 122 |
| H1B | -1049.48 | 8985.26 | 7978.29 | 122 |
| H1C | -14.15 | 9635.57 | 8433.78 | 122 |
| H25 | -1486.76 | 4863.66 | 4886.06 | 110 |
| H22A | 719.4 | 4375.73 | 1521.91 | 154 |
| H22B | 1225.91 | 4127.33 | 499 | 154 |
| H22C | 1105.77 | 5390.24 | 801.98 | 154 |

Furthermore, the interatomic bond length (unit: angstrom) is shown in Table 6.

TABLE 6

| Atom | Atom | Length/Å |
|---|---|---|
| Cl36 | C6 | 1.733(3) |
| F32 | C14 | 1.352(3) |
| O35 | C11 | 1.216(3) |
| O34 | C10 | 1.208(3) |
| O38 | C23 | 1.310(3) |
| N12 | C11 | 1.369(3) |
| N12 | C9 | 1.398(3) |
| N12 | C12 | 1.465(3) |
| F33 | C16 | 1.347(3) |
| N16 | C9 | 1.373(3) |
| N16 | C10 | 1.365(3) |
| N14 | C11 | 1.382(3) |
| N14 | C10 | 1.386(3) |
| N14 | C19 | 1.466(3) |
| N9 | N1 | 1.342(3) |
| N9 | C4 | 1.358(3) |
| N10 | C9 | 1.262(3) |
| N10 | C7 | 1.421(3) |
| N1 | C2 | 1.332(3) |
| N1 | C1 | 1.466(3) |
| F31 | C17 | 1.345(3) |
| N23 | N20 | 1.360(3) |
| N23 | C20 | 1.313(3) |
| N20 | C21 | 1.309(4) |
| N20 | C22 | 1.453(4) |
| N22 | C20 | 1.345(3) |
| N22 | C21 | 1.326(4) |
| O39 | C23 | 1.196(3) |
| C12 | C13 | 1.503(3) |
| C20 | C19 | 1.485(4) |
| C7 | C6 | 1.431(4) |
| C7 | C8 | 1.362(4) |
| C4 | C5 | 1.398(4) |
| C4 | C3 | 1.402(4) |
| C13 | C14 | 1.381(3) |
| C13 | C18 | 1.383(4) |
| C5 | C6 | 1.364(4) |
| C14 | C15 | 1.379(4) |
| C3 | C8 | 1.416(3) |
| C3 | C2 | 1.388(4) |

TABLE 6-continued

| Atom | Atom | Length/Å |
|---|---|---|
| C23 | C24 | 1.475(4) |
| O41 | C26 | 1.304(4) |
| C24 | C24[1] | 1.307(5) |
| C18 | C17 | 1.367(4) |
| C15 | C16 | 1.355(4) |
| C16 | C17 | 1.370(4) |
| O43 | C26 | 1.189(4) |
| C26 | C25 | 1.466(5) |
| C25 | C25[2] | 1.273(7) |

In the fumaric acid cocrystal Form I of the compound represented by Formula (I-B), one molecule of the compound represented by Formula (I-B) was present in the asymmetric unit. The structure of the fumaric acid cocrystal Form I of the compound represented by Formula (I-B) in the asymmetric unit is shown in FIG. 2.

The numbers of non-hydrogen atoms in Tables 3 to 4 and 6 correspond to the numbers shown in FIG. 2, respectively.

As shown in Table 6, the bond length of N10-C9 was about 1.26 Å, and the bond length of N16-C9 was about 1.37 Å.

Since the bond length of N10-C9 (about 1.26 Å) is shorter than that of N16-C9 (about 1.37 Å), the fumaric acid cocrystal Form I of the compound represented by Formula (I-B) was identified as imino structure:

[Chemical Formula 16]

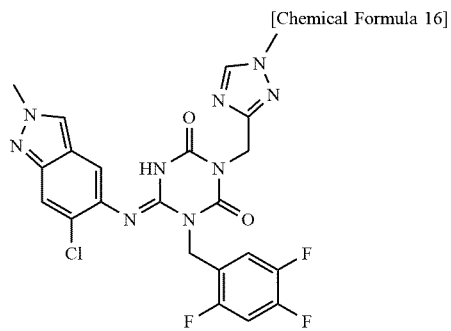

Further, the result of the powder X-ray diffraction of the fumaric acid cocrystal Form I of the compound represented by Formula (I-B) is shown.

In the powder X-ray diffraction pattern, peaks were observed at the diffraction angle (2θ): 7.8±0.2°, 9.5±0.2°, 10.1±0.2°, 10.9±0.2°, 13.8±0.2°, 14.7±0.2°, 18.6±0.2°, 22.6±0.2°, 23.5±0.2° and 24.6±0.2°.

In the powder X-ray diffraction pattern, the peaks of the diffraction angle (2θ): 9.5±0.2°, 10.9±0.2°, 18.6±0.2°, 23.5±0.2°and 24.6±0.2 are particularly characteristic as the fumaric acid cocrystal Form I of the compound represented by Formula (I-B).

The result of the Raman spectrum of fumaric acid cocrystal Form I of the compound represented by Formula (I-B) is shown in FIG. 3.

A major Raman spectrum peaks were observed at 637.3 cm$^{-1}$±2 cm$^{-1}$, 676.3 cm$^{-1}$ ±2 cm$^{-1}$, 688.8 cm$^{-1}$±2 cm$^{-1}$, 748.0 cm$^{-1}$±2 cm$^{-1}$, 758.1 cm$^{-1}$±2 cm$^{-1}$, 1029.3 cm$^{-1}$ ±2 cm$^{-1}$, 1114.4 cm$^{-1}$±2 cm$^{-1}$, 1281.3 cm$^{-1}$±2 cm$^{-1}$, 1332.1 cm$^{-1}$±2 cm$^{-1}$, 1374.4 cm$^{-1}$±2 cm$^{-1}$, 1456.0 cm$^{-1}$ ±2 cm$^{-1}$, 1515.5 cm$^{-1}$±2 cm$^{-1}$, 1636.0 cm$^{-1}$±2 cm$^{-1}$, 1665.7 cm$^{-1}$±2 cm$^{-1}$, 1715.7 cm$^{-1}$±2 cm$^{-1}$, 1739.1 cm$^{-1}$ ±2 cm$^{-1}$, 2951.2 cm$^{-1}$±2 cm$^{-1}$, 3068.3 cm$^{-1}$±2 cm$^{-1}$ and 3126.2 cm$^{-1}$±2 cm$^{-1}$.

In one embodiment, the fumaric acid cocrystal Form I of the compound represented by Formula (I-B) has a Raman spectrum peaks at 676.3 cm$^{-1}$±2 cm$^{-1}$, 748.0 cm$^{-1}$±2 cm$^{-1}$, 1029.3 cm$^{-1}$±2 cm$^{-1}$, 1374.4 cm$^{-1}$±2 cm$^{-1}$, 1515.5 cm$^{-1}$ ±2 cm$^{-1}$, 1665.7 cm$^{-1}$ ±2 cm$^{-1}$, 1715.7 cm$^{-1}$±2 cm$^{-1}$ and 1739.1 cm$^{-1}$±2 cm$^{-1}$.

In one embodiment, the fumaric acid cocrystal Form I of the compound represented by Formula (I-B) has a Raman spectrum peak at 676.3 cm$^{-1}$±2 cm$^{-1}$.

In one embodiment, the fumaric acid cocrystal Form I of the compound represented by Formula (I-B) has a Raman spectrum peak at 748.0 cm$^{-1}$±2 cm$^{-1}$.

In one embodiment, the fumaric acid cocrystal Form I of the compound represented by Formula (I-B) has a Raman spectrum peak at 1029.3 cm$^{-1}$±2 cm$^{-1}$.

In one embodiment, the fumaric acid cocrystal Form I of the compound represented by Formula (I-B) has a Raman spectrum peak at 1374.4 cm$^{-1}$±2 cm$^{-1}$.

In one embodiment, the fumaric acid cocrystal Form I of the compound represented by Formula (I-B) has a Raman spectrum peak at 1515.5 cm$^{-1}$±2 cm$^{-1}$.

In one embodiment, the fumaric acid cocrystal Form I of the compound represented by Formula (I-B) has a Raman spectrum peak at 1665.7 cm$^{-1}$±2 cm$^{-1}$.

In one embodiment, the fumaric acid cocrystal Form I of the compound represented by Formula (I-B) has a Raman spectrum peak at 1715.7 cm$^{-1}$±2 cm$^{-1}$.

In one embodiment, the fumaric acid cocrystal Form I of the compound represented by Formula (I-B) has a Raman spectrum peak at 1739.1 cm$^{-1}$±2 cm$^{-1}$.

In one embodiment, the fumaric acid cocrystal Form I of the compound represented by Formula (I-B) has one or more Raman spectrum peak(s) selected from the group consisting of: Raman spectral peak of 676.3 cm$^{-1}$±2 cm$^{-1}$, Raman spectral peak of 748.0 cm$^{-1}$±2 cm$^{-1}$, Raman spectral peak of 1029.3 cm$^{-1}$±2 cm$^{-1}$, Raman spectral peak of 1374.4 cm$^{-1}$ ±2 cm$^{-1}$, Raman spectral peak of 1515.5 cm$^{-1}$±2 cm$^{-1}$, Raman spectral peak of 1665.7 cm$^{-1}$±2 cm$^{-1}$, Raman spectral peak of 1715.7 cm$^{-1}$±2 cm$^{-1}$ and Raman spectral peak of 1739.1 cm$^{-1}$±2 cm$^{-1}$.

The DSC analysis result of the fumaric acid cocrystal Form I of the compound represented by Formula (I-B) is shown in FIG. 4. The onset temperature (endothermic peak) was about 272° C.

Example 3

To 200 mg of Compound (I-0115), 395 µL (1.05 eq) of a 1 mol/L aqueous solution of potassium hydroxide and 2 mL of acetonitrile were added, and the solvent was evaporated to dryness. 1 mL of ethyl acetate was added thereto, and the mixture was stirred at 60° C. for 10 minutes and then stirred overnight at 25° C. Solids were collected by filtration and dried to obtain a crystalline form of potassium salt Form I of the compound represented by Formula (I-B). With regard to the crystalline form of potassium salt Form I of the compound represented by Formula (I-B), the molecular structure (amino form / imino form) was not identified.

The results of powder X-ray diffraction of the crystalline form of potassium salt Form I of the compound represented by Formula (I-B) are shown in FIG. 5.

In the powder X-ray diffraction pattern, peaks were observed at the diffraction angles (2θ): 7.7±0.2°, 8.1±0.2°, 12.6±0.2°, 16.7±0.2°, 18.5±0.2°, 19.4±0.2°, 20.7±0.2°, 22.0±0.2°, 23.7±0.2°, and 25.3±0.2°.

Regarding the powder X-ray diffraction peaks, the peaks at the diffraction angles (2θ): 8.1±0.2°, 16.7±0.2°, 20.7±0.2°, 22.0±0.2°, 25.3±0.2° are particularly characteristic as the crystalline form of potassium salt Form I of the compound represented by Formula (I-B).

The results of Raman spectroscopy of the crystal of potassium salt Form I of the compound represented by Formula (I-B) are shown in FIG. 6.

Major Raman spectrum peaks were observed at 638.4 cm$^{-1}$±2 cm$^{-1}$, 676.3 cm$^{-1}$ ±2 cm$^{-1}$, 724.1 cm$^{-1}$±2 cm$^{-1}$, 749.1 cm$^{-1}$±2 cm$^{-1}$, 876.9 cm$^{-1}$±2 cm$^{-1}$, 1008.7 cm$^{-1}$±2 cm$^{-1}$, 1105.9 cm$^{-1}$±2 cm$^{-1}$, 1294.8 cm$^{-1}$±2 cm$^{-1}$, 1363.1 cm$^{-1}$±2 cm$^{-1}$, 1409.2 cm$^{-1}$±2 cm$^{-1}$, 1457.0 cm$^{-1}$±2 cm$^{-1}$, 1506.4 cm$^{-1}$±2 cm$^{-1}$, 1526.5 cm$^{-1}$±2 cm$^{-1}$, 1577.4 cm$^{-1}$±2 cm$^{-1}$, 1624.1 cm$^{-1}$±2 cm$^{-1}$, 1688.3 cm$^{-1}$±2 cm$^{-1}$, 2952.0 cm$^{-1}$±2 cm$^{-1}$, 2980.5 cm$^{-1}$±2 cm$^{-1}$, 3073.7 cm$^{-1}$±2 cm$^{-1}$, and 3121.6 cm$^{-1}$±2 cm$^{-1}$.

According to one embodiment, the crystalline form of potassium salt Form I of the compound represented by Formula (I-B) has Raman spectrum peaks at 749.1 cm$^{-1}$ ±2 cm$^{-1}$, 1008.7 cm$^{-1}$±2 cm$^{-1}$, 1363.1 cm$^{-1}$±2 cm$^{-1}$, 1506.4 cm$^{-1}$±2 cm$^{-1}$, 1577.4 cm$^{-1}$±2 cm$^{-1}$, and 1624.1 cm$^{-1}$±2 cm$^{-1}$.

Example 4

To 190 mg of Compound (1-0115), 46.4 mg (1.1 eq) of succinic acid and 3.8 mL of acetonitrile were added, and the mixture was stirred at room temperature for 1 hour. Solids were collected by filtration and dried to obtain succinic acid cocrystal Form I of the compound represented by Formula (I-B). With regard to the succinic acid cocrystal Form I of the compound represented by Formula (I-B), the molecular structure (amino form / imino form) was not identified.

The results of powder X-ray diffraction of the succinic acid cocrystal Form I of the compound represented by Formula (I-B) are shown in FIG. 7.

In the powder X-ray diffraction pattern, peaks were observed at the diffraction angles (2θ): 9.5±0.2°, 10.9±0.2°, 11.3±0.2°, 13.4±0.2°, 14.4±0.2°, 18.7±0.2°, 19.4±0.2°, 22.6±0.2°, 23.4±0.2°, and 24.4±0.2°.

Regarding the powder X-ray diffraction peaks, the peaks at the diffraction angles (2θ): 10.9±0.2°, 18.7±0.2°, 22.6±0.2°, 23.4±0.2°, and 24.4±0.2° are particularly characteristic as the succinic acid cocrystal Form I of the compound represented by Formula (I-B).

The results of Raman spectroscopy of succinic acid cocrystal Form I of the compound represented by Formula (I-B) is shown in FIG. 8.

Major Raman spectrum peaks were observed at 631.6 cm$^{-1}$±2 cm$^{-1}$, 676.4 cm$^{-1}$ ±2 cm$^{-1}$, 748.1 cm$^{-1}$±2 cm$^{-1}$, 812.3 cm$^{-1}$±2 cm$^{-1}$, 1025.2 cm$^{-1}$±2 cm$^{-1}$, 1114.6 cm$^{-1}$±2 cm$^{-1}$, 1229.2 cm$^{-1}$±2 cm$^{-1}$, 1331.3 cm$^{-1}$±2 cm$^{-1}$, 1374.6 cm$^{-1}$±2 cm$^{-1}$, 1515.7 cm$^{-1}$±2 cm$^{-1}$, 1636.3 cm$^{-1}$±2 cm$^{-1}$, 1665.0 cm$^{-1}$±2 cm$^{-1}$, 1712.1 cm$^{-1}$±2 cm$^{-1}$, 1737.5 cm$^{-1}$±2 cm$^{-1}$, 2953.3 cm$^{-1}$±2 cm$^{-1}$, 2982.6 cm$^{-1}$±2 cm$^{-1}$, 3069.5 cm$^{-1}$±2 cm$^{-1}$, and 3127.5 cm$^{-1}$±2 cm$^{-1}$.

According to one exemplary embodiment, the succinic acid cocrystal Form I of the compound represented by Formula (I-B) has Raman spectrum peaks at 676.4 cm$^{-1}$ ±2 cm$^{-1}$, 748.1 cm$^{-1}$±2 cm$^{-1}$, 1025.2 cm$^{-1}$±2 cm$^{-1}$, 1374.6 cm$^{-1}$±2 cm$^{-1}$, 1515.7 cm$^{-1}$±2 cm$^{-1}$, and 1665.0 cm$^{-1}$±2 cm$^{-1}$.

Example 5

750 µL of ethyl acetate was added to 150 mg of Compound (I-0115), and the mixture was stirred overnight at 60° C. Solids were collected by filtration and dried to obtain a crystalline form of anhydride Form I of the compound represented by Formula (I-B). With regard to the crystalline form of anhydride Form I of the compound represented by Formula (I-B), the molecular structure (amino form / imino form) was not identified.

The results of powder X-ray diffraction of the crystalline form of anhydride Form I of the compound represented by Formula (I-B) are shown in FIG. 9.

In the powder X-ray diffraction pattern, peaks were observed at the diffraction angles (2θ): 6.6±0.2°, 9.6±0.2°, 12.2±0.2°, 13.24-0.2°, 16.2±0.2°, 17.5±0.2°, 19.8±0.2°, 23.3±0.2°, 24.5±0.2°, and 26.1±0.2°.

Regarding the powder X-ray diffraction peaks, the peaks at the diffraction angles (2θ): 6.6±0.2°, 9.6±0.2°, 13.2±0.2°, 17.5±0.2°, and 19.8±0.2° are particularly characteristic as anhydride Form I of the compound represented by Formula (I-B).

The results of Raman spectroscopy of the crystal of anhydride Form I of the compound represented by Formula (I-B) are shown in FIG. 10.

Major Raman spectrum peaks were observed at 630.4 cm$^{-1}$±2 cm$^{-1}$, 672.8 cm$^{-1}$ ±2 cm$^{-1}$, 744.6 cm$^{-1}$±2 cm$^{-1}$, 805.4 cm$^{-1}$±2 cm$^{-1}$, 997.8 cm$^{-1}$±2 cm$^{-1}$, 1020.7 cm$^{-1}$±2 cm$^{-1}$, 1297.9 cm$^{-1}$±2 cm$^{-1}$, 1335.2 cm$^{-1}$±2 cm$^{-1}$, 1362.0 cm$^{-1}$±2 cm$^{-1}$, 1461.0 cm$^{-1}$±2 cm$^{-1}$, 1505.4 cm$^{-1}$±2 cm$^{-1}$, 1527.5 cm$^{-1}$±2 cm$^{-1}$, 1629.1 cm$^{-1}$±2 cm$^{-1}$, 1645.9 cm$^{-1}$±2 cm$^{-1}$, 1755.7 cm$^{-1}$±2 cm$^{-1}$, 2943.3 cm$^{-1}$±2 cm$^{-1}$, 2982.1 cm$^{-1}$±2 cm$^{-1}$, 3060.5 cm$^{-1}$±2 cm$^{-1}$, 3104.7 cm$^{-1}$±2 cm$^{-1}$, and 3123.2 cm$^{-1}$±2 cm$^{-1}$.

According to an exemplary embodiment, the crystal of anhydride Form I of the compound represented by Formula (I-B) has Raman spectrum peaks at 630.4 cm$^{-1}$ ±2 cm$^{-1}$, 744.6 cm$^{-1}$±2 cm$^{-1}$, 997.8 cm$^{-1}$±2 cm$^{-1}$, 1362.0 cm$^{-1}$±2 cm$^{-1}$, 1461.0 cm$^{-1}$±2 cm$^{-1}$, 1505.4 cm$^{-1}$±2 cm$^{-1}$, and 1755.7 cm$^{-1}$±2 cm$^{-1}$.

Example 6

To 95 mg of Compound (I-0115), 187 µL (1.05 eq) of a 1 mol/L aqueous solution of sodium hydroxide and 1 mL of acetonitrile were added, and the solvent was evaporated to dryness. 100 µL of acetonitrile was added to 5 mg of the obtained solids, and the mixture was stirred overnight at 25° C. Solids were collected by filtration and dried to obtain a crystal of sodium salt Form I of the compound represented by Formula (I-B). With regard to the crystal of sodium salt Form I of the compound represented by Formula (I-B), the molecular structure (amino form / imino form) was not identified.

The results of powder X-ray diffraction of the crystal of sodium salt Form I of the compound represented by Formula (I-B) are shown in FIG. 11.

In the powder X-ray diffraction pattern, peaks were observed at the diffraction angles (2θ): 6.6±0.2°, 8.1±0.2°, 10.9±0.2°, 11.6+0.2°, 13.2±0.2°, 16.0±0.2°, 22.1±0.2°, 23.4±0.2°, 26.6±0.2°, and 28.9±0.2°.

Regarding the powder X-ray diffraction peaks, the peaks at the diffraction angles (2θ): 8.1±0.2°, 10.9±0.2°, 13.2±0.2°, 23.4±0.2°, and 26.6±0.2° are particularly characteristic as the crystal of sodium salt Form I of the compound represented by Formula (I-B).

The results of Raman spectroscopy of the crystal of sodium salt Form I of the compound represented by Formula (I-B) are shown in FIG. 12.

Major Raman spectrum peaks were observed at 638.4 cm$^{-1}$±2 cm$^{-1}$, 675.1 cm$^{-1}$±2 cm$^{-1}$, 746.8 cm$^{-1}$±2 cm$^{-1}$, 1013.0 cm$^{-1}$±2 cm$^{-1}$, 1106.9 cm$^{-1}$±2 cm$^{-1}$, 1126.2 cm$^{-1}$±2 cm$^{-1}$, 1299.0 cm$^{-1}$±2 cm$^{-1}$, 1367.2 cm$^{-1}$±2 cm$^{-1}$, 1407.1 cm$^{-1}$±2 cm$^{-1}$, 1457.0 cm$^{-1}$±2 cm$^{-1}$, 1504.4 cm$^{-1}$±2 cm$^{-1}$, 1526.5 cm$^{-1}$±2 cm$^{-1}$, 1581.3 cm$^{-1}$±2 cm$^{-1}$, 1629.1 cm$^{-1}$±2 cm$^{-1}$, 1711.8 cm$^{-1}$±2 cm$^{-1}$, 2959.1 cm$^{-1}$±2 cm$^{-1}$, 3062.0 cm$^{-1}$±2 cm$^{-1}$, and 3125.5 cm$^{-1}$±2 cm$^{-1}$.

According to one exemplary embodiment, the crystal of sodium salt Form I of the compound represented by Formula (I-B) has Raman spectrum peaks at 746.8 cm$^{-1}$±2 cm$^{-1}$, 1013.0 cm$^{-1}$±2 cm$^{-1}$, 1367.2 cm$^{-1}$±2 cm$^{-1}$, 1504.4 cm$^{-1}$±2 cm$^{-1}$, 1526.5 cm$^{-1}$±2 cm$^{-1}$, and 1581.3 cm$^{-1}$±2 cm$^{-1}$.

The results of simultaneous differential thermal analysis and thermogravimetric analysis (TG/DTA) of the crystal of sodium salt Form I of the compound represented by Formula (I-B) are shown in FIG. 13. As a result, a weight loss of 8.1% accompanied by an endothermic peak was confirmed from about 72° C. to about 105° C.

From the above-described measurement results, it is expected that the crystal of sodium salt Form I of the compound represented by Formula (I-B) is a crystal including 2.5 to 3 water equivalents of water.

Biological Test Examples for the compounds of the present invention will be described below.

It is desirable that the compounds represented by Formula (I) according to the present invention are compounds having coronavirus 3CL protease inhibitory activity and inhibiting coronavirus 3CL proteases.

Specifically, in the evaluation method described below, the IC$_{50}$ is preferably 50 µM or less, more preferably 1 µM or less, and even more preferably 100 nM or less.

Test Example 1: Inhibitory Activity of Cytopathic Effect (CPE) in VeroE6 Cells Expressing Human TMPRSS2 (VeroE6/TMPRSS2 Cells)

Operational Procedure

Dilution and Dispensing of Sample to Be Tested

The sample to be tested is diluted in advance to an appropriate concentration with DMSO, and a 2- to 5-fold series of serial dilutions is prepared and then dispensed into a 384-well plate.

Dilution and Dispensing of Cells and SARS-CoV-2

VeroE6/TMPRSS2 cells (JCRB1819, 5×10$^3$ cells/well) and SARS-CoV-2 (100-300 TCID$_{50}$/well) are mixed in a medium (MEM, 2% FBS, penicillin-streptomycin), the mixture is dispensed into the wells in which the sample to be tested has been introduced, and then the cells are cultured for 3 days in a CO$_2$ incubator.

Dispensing of CellTiter-Glo® 2.0 and Measurement of Luminescence Signals

The plate that has been cultured for 3 days is returned to room temperature, subsequently CellTiter-Glo®2.0 is dispensed into each well, and the plate is mixed using a plate mixer. The plate is left to stand for a certain time, and then the luminescence signals (Lum) is measured with a plate reader.

Calculation of Each Measurement Item Value

Calculation of 50% SARS-CoV-2 Infected Cell Death Inhibitory Concentration (EC$_{50}$)

When x denotes the logarithmic value of the compound concentration and y denotes %Efficacy, the inhibition curve is approximated by the following Logistic regression equation, and the value of x when y = 50 (%) is inputted is calculated as EC$_{50}$.

$$y = min + (max - min)/\{1 + (X50/x)^\wedge Hill\}$$

%Efficacy = {(Sample - virus control) / (cell control - virus control)} * 100%
cell control: the average of Lum of cell control wells
virus control: the average of Lum of virus control wells
min: lower limit value of y-axis, max: upper limit value of y-axis, X50: x-coordinates of inflection point, Hill: slope of curve at midpoint between min and max The compounds of the present invention were tested essentially as described above. The results are shown in the following.

Compound I-0115 : 0.328 µM

Reference Example 1

Compounds I-0679, I-0683, I-0685 and I-1603 of WO2012/020749A (Patent Document 1), and Compounds I-575 and I-580 of WO2013/089212A (Patent Document 2), and Compound I-066 of WO2010/099266A (Patent Document 3) were tested essentially as described in Test Example 1. The results are shown in the tables below.

TABLE 7

| Structure | Patent Document 3 Compound 1-066 | Patent Document 1 Compound 1-1603 | Patent Document 1 Compound 1-0683 | Patent Document 1 Compound 1-0685 |
|---|---|---|---|---|
| EC50 [μM] | >50.0 | >50.0 | >50.0 | >50.0 |

TABLE 8

| | Patent Document 1 Compound I-0679 | Patent Document 2 Compound I-580 | Patent Document 2 Compound I-575 |
|---|---|---|---|
| Structure | | | |
| EC50 [μM] | >50.0 | >50.0 | >50.0 |

Compounds I-0679, I-0683, I-0685 and I-1603 of WO2012/020749A (Patent Document 1), and Compounds I-575 and I-580 of WO2013/089212A (Patent Document 2), and Compound I-066 of WO2010/099266A (Patent Document 3) did not show coronavirus replication inhibitory activity at concentrations up to 50 μM.

Test Example 2: Inhibitory Activity Test Against SARS-CoV-2 3CL Proteases

Materials

Commercially available Recombinant SARS-CoV-2 3CL Protease
Commercially available substrate peptide

```
Dabcyl-Lys-Thr-Ser-Ala-Val-Leu-Gln-Ser-Gly-Phe-Arg-Lys-Met-Glu(Edans)-NH2 (SEQ ID NO: 1)
```

Internal Standard peptide

```
Dabcyl-Lys-Thr-Ser-Ala-Val-Leu(13C6,15N)-Gln (SEQ ID NO: 2)
```

Dabcyl-Lys-Thr-Ser-Ala-Val-Leu(13C6,15N)-Gln can be synthesized with reference to documents (Atherton, E.; Sheppard, R. C., "In Solid Phase Peptide Synthesis, A Practical Approach", IRL Press at Oxford University Pres, 1989.; Bioorg. Med. Chem., Vol. 5, No. 9, 1997, pp. 1883-1891; and the like). An example will be shown below.

H-Lys-Thr-Ser-Ala-Val-Leu(13C6,15N)-Glu(resin)-OαOtBu (the Lys-side chain is Boc-protected, the Thr-side chain is protected with a tert-butyl group, the Ser-side chain is protected with a tert-butyl group, the C-terminal OH of Glu is protected with a tert-butyl group, and the carboxylic acid of the Glu-side chain is condensed into the resin) is synthesized by Fmoc solid-phase synthesis using a Rink amide resin.

Regarding the modification of the N-terminal Dabcyl group, 4-dimethylaminoazobenzene-4'-carboxylic acid (Dabcyl-OH) is condensed on the resin using EDC/HOBT. Final deprotection and cleavage from the resin are carried out by treatment with TFA/EDT = 95 : 5. Thereafter, purification is performed by reverse phase HPLC.

RapidFire Cartridge C4 type A

Operational Procedure

Preparation of Assay Buffer

In the present test, an assay buffer composed of 20 mM Tris-HCl, 100 mM sodium chloride, 1 mM EDTA, 10 mM DTT, and 0.01% BSA is used. For a compound with an $IC_{50}$ of 10 nM or less, an assay buffer composed of 20 mM Tris-HCl, 1 mM EDTA, 10 mM DTT, and 0.01% BSA is used.

Dilution and Dispensing of Sample to Be Tested

The sample to be tested is diluted in advance to an appropriate concentration with DMSO, and a 2- to 5-fold series of serial dilutions is prepared and then dispensed into a 384-well plate.

Addition of Enzyme and Substrate, and Enzymatic Reaction

To a prepared compound plate, 8 μM substrate, and a 6 or 0.6 nM enzyme solution are added, and incubation is carried out for 3 to 5 hours at room temperature. Thereafter, a reaction stopping solution (0.067 μM Internal Standard, 0.1% formic acid, and 10% or 25% acetonitrile) is added to stop the enzymatic reaction.

Measurement of Reaction Product

The plate in which the reaction has been completed is measured using RapidFire System 360 and a mass analyzer (Agilent, 6550 iFunnel Q-TOF), or RapidFire System 365 and a mass analyzer (Agilent, 6495C Triple Quadrupole). Solution A (75% isopropanol, 15% acetonitrile, 5 mM ammonium formate) and solution B (0.01% trifluoroacetic acid, 0.09% formic acid) are used as a mobile phase at the measurement.

The reaction product detected by the mass analyzer is calculated using RapidFire Integrator or an equivalent program capable of analysis and is taken as Product area value. Furthermore, the Internal Standard that has been detected at the same time is also calculated and is designated as Internal Standard area value.

Calculation of Each Measurement Item Value

Calculation of P/IS

The area values obtained in the previous items are calculated by the following formula, and P/IS is calculated.

$$P/IS = Product\ Area\ Value\ /\ Internal\ Standard\ Area\ Value$$

Calculation of 50% SARS-CoV-2 3CL Protease Inhibitory Concentration ($IC_{50}$)

When x denotes the logarithmic value of the compound concentration and y denotes %Inhibition, the inhibition curve is approximated by the following Logistic regression equation, and the value of x obtainable when y = 50 (%) is inputted is calculated as $IC_{50}$.

$$y = min + (max - min)/\{1 + (X50/x)^{\wedge}Hill\}$$

$$\%Inhibition = \{1-(Sample-Control(-))/Control(+)-Control(-))\}*100$$

Control(-):the average of P/IS of enzyme inhibited condition wells
Control(+):the average of P/IS of DMSO control wells
min: lower limit value of y-axis, max: upper limit value of y-axis, X50: x-coordinates of inflection point, Hill: slope of curve at midpoint between min and max The compounds of the present invention were tested essentially as described above. The results are shown in the following.

Compound 1-0115 : 0.010 μM

The preparation examples shown below are only for illustrative purposes and are by no means intended to limit the scope of the invention.

The compound of the present invention can be administered as a pharmaceutical composition by any conventional route, particularly enterally, for example, orally, for example, in the form of a tablet or a capsule; parenterally, for example, in the form of an injectable preparation or a suspension; and topically, for example, in the form of a lotion, a gel, an ointment or a cream, or as a pharmaceutical composition in a transnasal form or a suppository form. A pharmaceutical composition comprising the compound of the present invention in a free form or in the form of a pharmaceutically acceptable salt together with at least one pharmaceutically acceptable carrier or diluent can be produced by a mixing, granulating, or coating method in a conventional manner. For example, the oral composition can be a tablet, a granular preparation, or a capsule, each containing an excipient, a disintegrating agent, a binder, a lubricating agent, and the like, as well as an active ingredient and the like. Furthermore, the composition for injection can be prepared as a solution or a suspension, may be sterilized, and may contain a preservative, a stabilizer, a buffering agent, and the like.

INDUSTRIAL APPLICABILITY

The compound according to the present invention has coronavirus 3CL protease inhibitory activity, and it is considered that the compound is useful as a therapeutic agent and/or a prophylactic agent for a disease or a condition associated with coronavirus 3CL proteases.

The invention claimed is:
1. A compound represented by the following Formula:

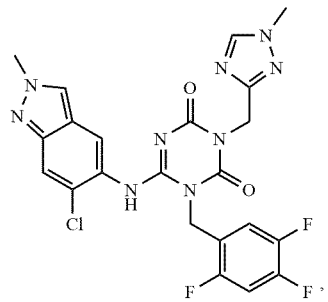

or a pharmaceutically acceptable salt thereof.

2. A pharmaceutical composition comprising the compound according to claim 1, or a pharmaceutically acceptable salt thereof, and a pharmaceutically acceptable carrier or diluent.

3. A coronavirus 3 CL protease inhibitor comprising the compound according to claim 1, or a pharmaceutically acceptable salt thereof.

4. A coronavirus replication inhibitor comprising the compound according to claim 1, or a pharmaceutically acceptable salt thereof.

5. The coronavirus replication inhibitor according to claim 4, wherein the coronavirus is an alphacoronavirus and/or betacoronavirus.

6. The coronavirus replication inhibitor according to claim 4, wherein the coronavirus is SARS-CoV-2.

7. A method for treating and/or preventing a disease associated with coronavirus 3 CL proteases, comprising administering an effective amount of the compound according to claim 1, or a pharmaceutically acceptable salt thereof, to a patient in need thereof.

8. The compound according to claim 1, or a pharmaceutically acceptable salt thereof, for use in treating and/or preventing a disease associated with coronavirus 3CL proteases.

9. A complex comprising a compound represented by Formula (I-B):

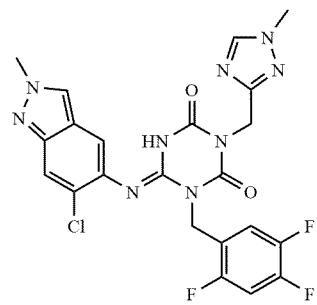

and fumaric acid.

10. The complex according to claim 9, wherein the compound represented by Formula (I-B):

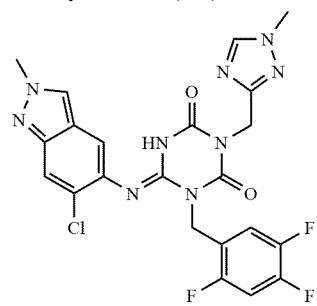

and fumaric acid are present in a molar ratio of 1:1.

11. The complex according to claim 9, which is a fumaric acid cocrystal Form I.

12. The fumaric acid cocrystal Form I according to claim 11, which exhibits a powder X-ray diffraction pattern having peaks at diffraction angles (2θ): 9.5 ± 0.2°, 10.9 ± 0.2°, 18.6 ± 0.2°, 23.5 ± 0.2° and 24.6 ± 0.2°.

13. The fumaric acid cocrystal Form I according to claim 11, which exhibits a powder X-ray diffraction pattern having peaks at diffraction angles (2θ): 7.8 ± 0.2°, 9.5 ± 0.2°, 10.1 ± 0.2°, 10.9 ± 0.2°, 13.8 ± 0.2°, 14.7 ± 0.2°, 18.6 ± 0.2°, 22.6 ± 0.2°, 23.5 ± 0.2° and 24.6 ± 0.2°.

14. The fumaric acid cocrystal Form I according to claim 11, which exhibits a Raman spectrum having Raman spectral peaks: 676.3 cm$^{-1}$±2 cm$^{-1}$, 748.0 cm$^{-1}$±2 cm$^{-1}$, 1029.3cm$^{-1}$ ±2 cm$^{-1}$, 1374.4 cm$^{-1}$±2 cm$^{-1}$, 1515.5 cm$^{-1}$±2 cm$^{-1}$, 1665.7 cm$^{-1}$±2 cm$^{-1}$, 1715.7 cm$^{-1}$±2 cm$^{-1}$ and 1739.1 cm$^{-1}$ ±2 cm$^{-1}$.

15. A pharmaceutical composition comprising the fumaric acid cocrystal Form I according to claim 11.

* * * * *